(12) United States Patent
Ikushima et al.

(10) Patent No.: US 9,901,280 B2
(45) Date of Patent: Feb. 27, 2018

(54) APPARATUS FOR MEASURING PROPERTIES OF AN OBJECT WITH ACOUSTICALLY INDUCED ELECTROMAGNETIC WAVES

(75) Inventors: Kenji Ikushima, Kawasaki (JP); Susumu Komiyama, Setagaya-ku (JP)

(73) Assignee: JAPAN SCIENCE AND TECHNOLOGY AGENCY, Saitama (JP)

(*) Notice: Subject to any disclaimer, the term of this patent is extended or adjusted under 35 U.S.C. 154(b) by 1404 days.

(21) Appl. No.: 12/093,036

(22) PCT Filed: Aug. 14, 2006

(86) PCT No.: PCT/JP2006/316028
§ 371 (c)(1),
(2), (4) Date: Mar. 5, 2009

(87) PCT Pub. No.: WO2007/055057
PCT Pub. Date: May 18, 2007

(65) Prior Publication Data
US 2009/0221900 A1    Sep. 3, 2009

(30) Foreign Application Priority Data
Nov. 9, 2005    (JP) .................... 2005-325064

(51) Int. Cl.
*A61B 5/05*    (2006.01)
*A61B 5/00*    (2006.01)
(Continued)

(52) U.S. Cl.
CPC .............. *A61B 5/05* (2013.01); *A61B 5/0093* (2013.01); *A61B 5/4064* (2013.01);
(Continued)

(58) Field of Classification Search
USPC .................. 600/407; 324/223–224, 247–248
See application file for complete search history.

(56) References Cited

U.S. PATENT DOCUMENTS 3,809,070 A * 5/1974 Doll et al. .................... 600/409
4,309,905 A    1/1982 Maizenberg et al.
(Continued)

FOREIGN PATENT DOCUMENTS

JP    63-311185 A    12/1988
JP    01-307681 A    12/1989
(Continued)

OTHER PUBLICATIONS

International Search Report (ISR) for PCT/JP2006/316028 for Examiner consideration.
(Continued)

*Primary Examiner* — Joel F Brutus

(57) ABSTRACT

A measuring method and apparatus in which a measurable object (23) is irradiated with acoustic waves to measure a change in property value of charged particles in the object from electromagnetic waves induced thereby. A part (2) of the measurable object irradiated with an acoustic focused beam (1) is in a charge distribution state in which positive charged particles (3) are greater in number in the part (2) where electromagnetic waves induced by positive charged particles (3) are not canceled by those induced by negative charged particles (4) and where net electromagnetic waves (6) are induced. Since a change in concentration of positive charged particles (3) and/or negative charged particles (4) changes the intensity of electromagnetic waves (6), it is possible to know such a change in concentration of the charged particles from a change in intensity of electromagnetic waves (6).

9 Claims, 17 Drawing Sheets

(51) Int. Cl.
A61B 8/00 (2006.01)
G01R 33/02 (2006.01)
G01R 33/035 (2006.01)
G01R 33/12 (2006.01)

(52) U.S. Cl.
CPC .......... *A61B 5/7203* (2013.01); *A61B 5/7225* (2013.01); *A61B 5/7228* (2013.01); *A61B 5/7235* (2013.01); *A61B 8/00* (2013.01); *G01R 33/0213* (2013.01); *G01R 33/035* (2013.01); *G01R 33/1269* (2013.01); *A61B 2562/0223* (2013.01); *A61B 2562/18* (2013.01)

(56) References Cited

U.S. PATENT DOCUMENTS

| | | | |
|---|---|---|---|
| 5,168,224 A * | 12/1992 | Maruizumi et al. | 324/300 |
| 5,170,666 A * | 12/1992 | Larsen | 73/571 |
| 6,216,025 B1 | 4/2001 | Kruger | |
| 7,165,451 B1 | 1/2007 | Brooks et al. | |
| 2002/0035327 A1 | 3/2002 | Kruger | |
| 2002/0050815 A1* | 5/2002 | Suzuki et al. | 324/248 |
| 2002/0094531 A1 | 7/2002 | Zenhausern | |
| 2003/0133596 A1* | 7/2003 | Brooks | 382/115 |
| 2003/0230344 A1* | 12/2003 | Ellson et al. | 137/391 |
| 2005/0046858 A1 | 3/2005 | Hanson et al. | |

FOREIGN PATENT DOCUMENTS

| | | |
|---|---|---|
| JP | H4-32788 A | 2/1992 |
| JP | H06-265529 A | 9/1994 |
| JP | 08-193982 A | 7/1996 |
| JP | H08-193982 A | 7/1996 |
| JP | 2824860 B2 | 11/1998 |
| JP | 2002-524176 A | 8/2002 |
| JP | 2002-286619 A | 10/2002 |
| JP | 2005-114595 A | 4/2005 |
| WO | 00/15097 A3 | 3/2000 |

OTHER PUBLICATIONS

PCT/ISA/237 in PCT/JP2006/316028 and its translation of Section V.

Michikazu Matsumura, "Invitation to Brain Science (The secret of a neural circuit is expounded)" (in Japanese) Science Co., Ltd., Jul. 10, 2003, first Ed. third print issue, pp. 55-65. Mentioned on p. 1 of the as-filed translation of the specification as concise explanation of relevance.

M. I. Posner & M. E. Raichele (translated into Japanese by Yoro, et al.) "Observing the Brain—The riddle of the mind that the cognitive neuroscience reveals" Nikkei Science Co., Ltd., Jun. 25, 2002, third print issue. pp. 82-99. Mentioned on p. 1 of the as-filed translation of the specification as concise explanation of relevance.

Michikazu Matsumura, "Invitation to Brain Science (The secret of a neural circuit is expounded)" (in Japanese) Science Co., Ltd., Jul. 10, 2003, first Ed. third print issue, p. 173. Mentioned on p. 2 of the as-filed translation of the specification as concise explanation of relevance.

Michikazu Matsumura, "Invitation to Brain Science (The secret of a neural circuit is expounded)" (in Japanese) Science Co., Ltd., Jul. 10, 2003, first Ed. third print issue, pp. 168-169. Mentioned on p. 2 of the as-filed translation of the specification as concise explanation of relevance.

"EDAP TMS-ESWL Sonolith", EDAP TMS, "http://www.edap-tms.com/en_US/products-services/sonolith-eswl.html", 1 page, printed from the Internet on Feb. 15, 2009. Mentioned on p. 3 of the as-filed translation of the specification as concise explanation of relevance.

"Ablatherm (R) Hifu, minimally-invasive treatment for localized prostate cancer", Ablatherm (R) Hifu, "http://www.edap-tms.com/en_US/products-services/ablatherm-hifu.html", 2 pages, printed from the Internet on Feb. 15, 2009. Mentioned on p. 3 of the as-filed translation of the specification as concise explanation of relevance.

Beaurepaire, et al., "Coherent terahertz emission from ferromagnetic films excited by femtosecond laser pulses", Applied Physics Letters, vol. 84, No. 18, pp. 3465-3467, May 3, 2004.

Translation of PCT/ISA/237, IB338, and IB373 of PCT/JP2006/316028.

U.S. Appl. No. 13/445,786, filed Apr. 12, 2012.

Japanese Office Action dated Aug. 9, 2011, in a counterpart Japanese Patent Application No. 2007-544069.

European Search Report dated Jan. 25, 2013, in a counterpart European patent application No. 06796418.9.

Japanese Office Action dated Jul. 16, 2013, in a counterpart Japanese patent application No. 2011-221814. (Partial translation of the Office Action is attached as a concise explanation of relevance.).

Joseph, "Wave Propagation in Piezoelectric Crystals", Acoustical Society of America, 1949, vol. 21, No. 3, pp. 159-167.

Thompson et al., "Electromagnetic excitation of high frequency acoustic waves and detection in the liquid phase", Analyst, 2003, vol. 128, pp. 1048-1055.

Japanese Office Action dated Oct. 1, 2013, in a counterpart Japanese patent application No. 2011-221814. (Partial translation of the Office Action is attached as a concise explanation of relevance.).

Homer et al., "Studies on the Origin of Sonically Induced Narrowing of Solid-state Nuclear Magnetic Resonance Spectra", J. Chem. Soc., 1993, vol. 89, No. 16, pp. 3029-3038 (Cited in Japanese Office Action above.).

The Non-Final Office Action for the child U.S. Appl. No. 13/445,786 dated Nov. 21, 2014.

Solovarov, "Acoustic nuclear magnetic resonance in the case of direct generation of sound in metals", Sov. Phys.—JETP, vol. 42, No. 1, pp. 141-144 (Listed by the U.S. Examiner in a PTO-892 form in the child U.S. Appl. No. 13/445,786.).

Final Office Action for U.S. Appl. No. 13/445,786 (a divisional of this application), dated Nov. 21, 2016.

K. D. Kihm et al. "Near wall-hindered Brownian diffusion of nanoparticles examined by three-dimensional retiometric total internal reflection fluorescence microscopy (3-D R-TIRFM)", Experiments in Fuids 37 (2004) pp. 811-824, Sep. 24, 2004.

E. A. Turov et al. "Nuclear Magnetic Resonance in Ferro- and Antiferromagnetics(1969)", 1972, pp. 156-165, Isreal program for scientific translations, Halsted Press, New York.

Wada, "Acoustic Paramagnetic Resonance", Acoustic properties of materials, Aug. 20, 1969, pp. 150-153, Kyoritsu Shuppan Co., Ltd., Tokyo, Japan.

European Patent Office, Examination Report for EP Patent Application No. 13197371.1, Oct. 6, 2015.

The Final Office Action for the child U.S. Appl. No. 13/445,786, dated Sep. 3, 2015.

The Non-Final Office Action for the child U.S. Appl. No. 13/445,786, dated Mar. 10, 2016.

Advisory Action for U.S. Appl. No. 13/445,786 (a divisional of this application), dated Mar. 29, 2017.

* cited by examiner

APPARATUS FOR MEASURING PROPERTIES OF AN OBJECT WITH ACOUSTICALLY INDUCED ELECTROMAGNETIC WAVES

TECHNICAL FIELD

The present invention relates to a method of and an apparatus for measuring properties of an object of every sort, including a human body, which when acoustically vibrated may be capable of emitting electromagnetic waves, from such electromagnetic waves induced by applicable sound waves. The present invention relates in particular to a technique using such a method for the measurement of an active site of a brain.

BACKGROUND ART

In the interest of elucidating a relation between a human mental activity and a brain's action and in an effort to specify a lesion in brain's disease therapeutics, attempts have been made to identify a neural active site of the brain. Neurons in a neural activity control an ion concentration to form a charge distribution and transmit information through propagation of a potential created by the charge distribution, namely of an action potential (see Non-patent Reference 1). Thus, the most direct information source that can identify a site of neural activity is the action potential, more cardinally the charge distribution which the neuron creates.

While in the measurement of an action potential in the nervous system, a method is usually taken in which to directly insert an electrode into the body, use cannot be made of this method for a human body, inter alia for its brain tissue but necessarily of a noninvasive measuring method to identify an active region from the outside of the human body without harming the body part.

As the noninvasive method of measuring a neural activity, PET (positron emission tomography; see Non-patent Reference 2), fMRI (functional magnetic resonance imaging; see Non-patent Reference 3), near infrared topography (see Non-patent Reference 4) and magneto-encephalography (see Non-patent Reference 5) have been primarily put to practical utilization at present.

In any of PET, fMRI and near infrared topography, however, in which neuron's activity is indirectly detected from a change in amount of metabolism, namely in amount of bloodstream in the blood or oxygen therein, in the region of an active site, no electrical signal created by neurons is directly measured. As a result, their position and time resolutions for an active site are not sufficient in elucidating a relation between a human mental activity and a brain's action or in serving for disease therapy. They require a cyclotron accelerator for producing positrons, a high field generating apparatus for nuclear magnetic resonance or the like and are extremely high in apparatus cost.

Magneto-encephalography which detects a very weak magnetic field as induced by an intracellular electric current is a process that is high in time resolution as it detects neurons' activity more directly than do the others above. This method in which a position is estimated on the basis of a magnetic field distribution and hence determined indirectly is not enough in position resolution. Especially if a plurality of sites are active simultaneously, their identification then becomes difficult. There is also the problem that it is difficult to detect information from a deep part and an electric current passed towards a normal to a surface.

Included in properties of a material is a magnetic property. As regards the magnetization of a magnetic material, it is reported in Non-patent Reference 8, for example, that a ferromagnetic thin film irradiated with laser light of femtoseconds is observed to produce a coherent radiation in a THz band.

Non-patent Reference 1: Michikazu Matsumura "Invitation to Brain Science (The secret of a neural circuit is expounded)" (in Japanese) Science Co., Ltd., Jul. 10, 2003, first Ed. third print issue, pp. 55-65;

Non-patent Reference 2: M. I. Posner & M. E. Raichele (translated into Japanese by Takeshi Yoro, Masako Kato and Kiyoto Kasai) "Observing the Brain—The riddle of the mind that the cognitive neuroscience reveals" (in Japanese) Nikkei Science Co., Ltd., Jun. 25, 2002, third print issue;

Non-patent Reference 3: P. Jezzard, P. M. Matthews, S. M. Smith edited "Functional Mri: An Introduction & Methods", Oxford Univ. Pr (Sd), ISBN: 01985277 3X, (2003/06);

Non-patent Reference 4: Michikazu Matsumura "Invitation to Brain Science (The secret of a neural circuit is expounded)" (in Japanese) Science Co., Ltd., Jul. 10, 2003, first Ed. third print issue, p. 173;

Non-patent Reference 5: Michikazu Matsumura "Invitation to Brain Science (The secret of a neural circuit is expounded)" (in Japanese) Science Co., Ltd., Jul. 10, 2003, first Ed. third print issue, pp. 168-169;

Non-patent Reference 6: http://www.rofuku.go.jp/hanasi/es-w1.htm;

Non-patent Reference 7: http://www.edap-hifu.com/; and

Non-patent Reference 8: E. Beaurepaire and five others, Appl. Phys. Lett., Vol. 84, No. 18, pp. 3465-3467, May 3, 2004.

DISCLOSURE OF THE INVENTION

Problems to be Solved by the Invention

Identifying an active site in a brain that is related to a particular mental activity is an extremely effective means for elucidating a relation between a human mental activity and a brain's action, and determining in a therapy of a brain's disease if the activity of a particular site in a brain is normal or abnormal is extremely important to cure the brain's disease.

As will have been appreciated from the description above, however, the problem remains that neither the prior-art method of detecting a change in amount of metabolism in the blood to indirectly determine an active site nor the prior-art method of detecting a very weak magnetic field as induced by an intracellular electric current with the excitation of a neuron is sufficient in position resolution, and they are incapable of identifying an active site with necessity and sufficiency and yet are extremely high in apparatus cost.

In view of the problems mentioned above, it is an object of the present invention to provide a method of and an apparatus for measuring a change in property value of charged particles in an object, from electromagnetic waves induced by irradiating the object with acoustic waves, namely from acoustically induced electromagnetic waves and, in particular, a process of determining an active site in a brain to which the method is applied and which is capable of detecting a neuron's charge distribution which is representative of the most direct quantity of a neuron's activity to identify the active site in the brain at a high position resolution.

Means for Solving the Problem

As viewed microscopically, an object or substance necessarily comprises particles with positive charges and those with negative charges which as a whole are neutral. For instance, Si crystal is made up of a Si core having positive charges and electrons revolving around the core and having negative charges, which are neutral as a whole. An ionic crystal is made up of cations and anions which as a whole are neutral. A colloidal solution consists of colloidal particles with positive or negative charges and ions or molecules surrounding a colloidal particle and with charges opposite in sign to those of the colloidal particle which in toto are neutral. Further, a biological liquid in a living organism comprises cations such as of Na, K or the like and anions of Cl or the like which are neutral as a whole.

The particles which make up a part of an object which is irradiated with acoustic waves are caused to oscillate harmonically at an acoustic frequency and, based on the harmonic oscillations of their charges, the charged particles generate electromagnetic waves at the acoustic frequency. Thus, a change if any in concentration between charged particles in a part irradiated with acoustic waves cause a change in strength of the electromagnetic waves. By the way, since an object is neutral as a whole, if there exist positive charged particles there also exist negative charged particles of the same number and since electromagnetic waves generated by positive charged particles and those generated by negative charged particles are different by $\pi$ in phase and canceled by each other, it is apt to be considered that no electromagnetic wave is radiated from the object. Such a situation is rare, however. Even if in the part irradiated with acoustic waves there exist positive charged particles and negative charged particles in the same concentration, a difference between the positive and negative charged particles in their mass, size, shape, or number of charges or in interaction force of their surrounding medium, namely in their property value, makes a difference in amplitude between their harmonic oscillations, thus making a difference in strength between the electromagnetic waves they produce which are not fully canceled out by each other but emitted externally.

Thus, if a change has occurred in strength of electromagnetic waves radiated from the part of an object irradiated with sound waves, it means that any one of concentrations, masses, sizes, shapes, and numbers of charges of charged particles and interaction forces of their surrounding medium or in a plurality of these property values of the charged particles have been changed. That conversely, a change in such property value of the charged particles can be determined from a change in strength of the electromagnetic waves. And, on what change in proper values the change is based can be narrowed down on the basis of other information on the object irradiated with sound waves. For example, assuming that the state is that the masses, sizes, shapes, numbers of charges and interaction forces with surrounding media cannot be altered, a change in strength of the electromagnetic waves can be tied to a change in concentration of charged particles in the part of an object irradiated with acoustic waves.

Especially, in the case of a neuron when it is activated, a channel for Na ions on a cell wall is opened through which Na ions outside of a cell are diffused into the cell under their concentration gradient to form a distribution of Na ion charges, focusing sound waves on such a part to measure a strength of electromagnetic waves allows the strength of the electromagnetic waves to largely vary with a neuron's action and permits detecting the neuron's action directly. Likewise, when a muscle tissue of a living body is made active where a charge distribution for Ca ions is created, focusing acoustic waves on such a part to measure an intensity of electromagnetic waves allows the active site of muscle tissue to be detected directly.

The present invention has been made based on principles as mentioned above and will be described in detail hereinafter.

Accordingly, there is provided in accordance with the present invention a method of measuring a property of an object with acoustically induced electromagnetic waves, characterized in that it comprises the steps of: irradiating a measurable object with acoustic waves; and measuring electromagnetic waves generated from the measurable object to determine any one of properties of the object, including its electrical, magnetic and electromagnetic mechanical properties, from any one or a combination of strength, phase and frequency characteristics of the electromagnetic waves.

In the method mentioned above, the electric property determined of the measurable object preferably includes a change or changes in one or more of property values for electric field, dielectric constant, spatial gradient of electric field and spatial gradient of dielectric constant and for concentration, mass, size, shape and number of charges of charged particles which the measurable object possesses and for interaction with a medium surrounding the charged particles. The magnetic property determined of the measurable object preferably includes a property value for magnetization due to electron spin or nuclear spin in the measurable object or for acousto-magnetic resonance attributable to electron spin or nuclear spin in the measurable object. The electromagnetic mechanical property preferably includes a piezoelectric property or magnetostriction property of the measurable object.

According to the object's property measuring method of the present invention, if a change has occurred in a property value of charged particles contained in a part of the object irradiated with acoustic waves, namely in concentration, mass, seize, shape and number of charges of charged particles or interaction force with their surrounding medium or in a plurality of such property values, it is possible to determine any of electric property, magnetic property or electromagnetic mechanical property from a change in intensity, phase or frequency characteristic of electromagnetic waves which then occur and can be detected. For example, if there could be no possibility of change other than in the concentration of charged particles, a change in intensity of electromagnetic waves can be tied to a change in the concentration of charged particles. Also, if there could be no possibility of change other than in the interaction force with the medium surrounding the charged particles, a change in intensity of electromagnetic waves can be tied to a change in polarizability of electrons or cations in the charged particles. Further, as a magnetic property of the measurable object, magnetization due to electron spin or nuclear spin, or acousto-magnetic resonance due to electron spin or nuclear spin can be measured, and as an electromagnetic mechanical property, piezoelectric or magnetostriction property of the measurable object can be measured.

The acoustic waves with which the measurable object is irradiated may be in the form of acoustic wave pulses and the electromagnetic waves can be measured of time dependence of their intensity detected subsequent to irradiation with the acoustic wave pulses to determine a relaxation characteristic of a property value for charged particles which the measurable object possesses.

The acoustic waves can be in the form of those of a fixed frequency in a narrow band or acoustic wave pulses of a fixed frequency in a narrow band. The electromagnetic waves can then be measured at a high sensitivity, preferably by heterodyne or phase detection of the electromagnetic waves radiated from the measurable object with a frequency of the acoustic waves as a reference signal. Then, external noises having other frequency components can be excluded to allow detecting even a change very small in intensity of electromagnetic waves.

The acoustic waves of a fixed frequency in a narrow band can be in the form of pulses. Then, the electromagnetic waves are measured by heterodyne or phase detection of the electromagnetic waves radiated from the measurable object with a frequency of the acoustic waves as a reference signal and heterodyne or phase detection of a signal resulting from the said detection with a pulse frequency of the said pulses. In this case, too, external noises having other frequency components can further be excluded to allow detecting even a change extremely small in intensity of electromagnetic waves.

Preferably, from phase information of the phase detection it is determined in which of positive charged particles or negative charged particles that the object possesses the electromagnetic waves as a signal are originated. Using the phase detection allows it to be determined from phase information in which of positive charged particles or negative charged particles that the object possesses the electromagnetic waves as a signal are originated.

A signal of said electromagnetic waves can be measured that is isolated with respect to time from electromagnetic noises occurring at a source of emission of said acoustic wave pulses if a time period for a said acoustic wave pulse to propagate over a distance between the emission source of said acoustic wave pulses and said measurable object is chosen to be longer than a pulse duration of said acoustic wave pulse or if the said pulse duration is made shorter than the said time period for the acoustic wave pulse to propagate, thus allowing detection of a change very small in intensity of electromagnetic waves.

The measurable object is irradiated with acoustic waves preferably by focusing acoustic waves from a plurality of a source on a desired small part of the measurable object and electromagnetic waves induced at the small part are measured with an antenna or coil means disposed to surround the measurable object. Then, acoustic waves can be focused on a desired part and on the desired part from a desired direction and electromagnetic waves radiated from a desired position and from the desired positions towards a desired direction can be measured while their radiation bearing distribution can be determined. When an object is irradiated with acoustic waves, anisotropy in elasticity modulus of charged particles contained in the object may allow electromagnetic waves to be radiated in a direction different from that perpendicular to that of the acoustic oscillations. Then, measuring the radiation bearing distribution allows the type of charged particles and a change in the property value to be determined.

Preferably, focusing acoustic waves is scanned over a two-dimensional surface or three-dimensional volume of the measurable object and an intensity of induced electromagnetic waves at each scanning position is measured using an antenna or coil means surrounding the measurable object to determine a two-dimensional or three-dimensional distribution of changes in a property value of charged particles of the object by comparing the scanned position and the intensity of the measured electromagnetic waves.

The acoustic waves are preferably applied in the form of broadband ultrashort pulses composed of a plurality of frequency components. Then, the frequency of the electromagnetic waves can be measured so that from the measured frequency of electromagnetic waves, information may be derived on depthwise position of charged particles generating the electromagnetic waves inasmuch as acoustic waves higher in frequency damp faster and those lower in frequency arrive deeper in a brain or a muscle tissue of a living body. For example, it is possible to enhance the accuracy in depthwise position information of the acoustic wave focused part.

If the measurable object is a nervous tissue representative of a brain, a charge distribution can be formed when neuron is activated and if it is a muscle tissue of a living body, a charge distribution can likewise be formed when the muscle tissue is activated. Since the intensity of electromagnetic waves grow with the charge distribution, a two-dimensional or three-dimensional map of the activated site of brain or muscle tissue can be prepared if acoustic focusing is scanned over a two-dimensional surface or three-dimensional volume of the brain or muscle tissue, the intensity of electromagnetic waves induced at each scanning position is measured with the antenna or coil means disposed to surround the brain or muscle tissue and each scanning position and each measured intensity of electromagnetic waves are made corresponding to each other.

The method mentioned above is not limited to an object if it is a living body but can be applied to an object of any one of materials selected from the group which consists of colloidal solution, liquid crystal, solid electrolyte, ionic crystal, semiconductor, dielectric, metal, magnetic material and magnetic fluid or a composite material thereof or a structure or a functional device composed of such a material, in which a change in property value of charged particles can be measured to aid in clarifying the related phenomena.

The present invention also provides an apparatus for measuring a property of an object with acoustically induced electromagnetic waves, characterized in that it comprises an anechoic chamber, a retainer table for holding a measurable object disposed in the anechoic chamber, an acoustic generator disposed adjacent or in contact with the object, an antenna or coil means for receiving electromagnetic waves generated from a part which is irradiated with acoustic waves or pulses produced by the acoustic generator, and a control, measure and process unit for driving and controlling the acoustic generator and for measuring and processing electromagnetic waves received by the antenna or coil means.

The acoustic generator preferably comprises a plurality of acoustic generators whereby acoustic wave pulses generated from the acoustic generators are controlled of their mutual phase by the control, measure and process unit so as to be focused on a desired position of said measurable object and the focusing position of acoustic waves is scanned over a two-dimensional surface or three-dimensional volume of the measurable object.

The acoustic generator may comprise a plurality of acoustic generators fixed on a concaved surface whose normal is focused on a point. Then, the control, measure and process unit preferably drives these acoustic generators simultaneously to generate acoustic wave pulses and at the same time causes the acoustic generators fixed on the concaved surface to scan mechanically around the measurable object whereby the focusing position of acoustic waves is scanned over a two-dimensional surface or three-dimensional volume of the measurable object.

The control, measure and process unit preferably includes a means by which electromagnetic waves received by the antenna or coil means are heterodyne- or phase-detected with a frequency of the acoustic waves or a pulse frequency of the acoustic wave pulses. Then, external noises possessed by other frequency components can be excluded to allow a change very small in intensity of electromagnetic waves to be detected.

A means is preferably included by which an electromagnetic wave signal resulting from detection by the said detecting means is locked in with a pulse frequency of the acoustic wave pulses. Then, external noises possessed by other frequency components can be excluded more to allow a change very small in intensity of electromagnetic waves to be detected.

The control, measure and process unit preferably comprises a means for causing broadband ultrashort pulses to be generated from the acoustic generator and a means for measuring a frequency of electromagnetic waves received by the antenna or coil means. Then, it is possible to enhance accuracy in depth-wise position information of the acoustic wave focused part.

The means for measuring a frequency of electromagnetic waves preferably comprises a bandpass filter provided in the control, measure and process unit.

The means for measuring a frequency of electromagnetic waves may also comprise a bandpass filter and a lock-in amplifier provided in the control, measure and process unit. Then, external noises possessed by other frequency components can further be excluded to allow a frequency of electromagnetic waves to be detected even if their intensity is very small.

The means for measuring a frequency of electromagnetic waves may also comprise a spectrum analyzer provided in the control, measure and process unit. Then, Fourier transformation by the spectrum analyzer of electromagnetic waves allow the intensity for each of frequency components of electromagnetic waves to be detected and the frequency of electromagnetic waves to be determined from the frequency component exhibiting the maximum intensity.

Effects of the Invention

According to the method and apparatus of the present invention, irradiating a measurable object with acoustic waves followed by measuring electromagnetic waves generated from the measurable object allows any one of electric, magnetic and electromagnetic mechanical properties of the measurable object to be determined from any one or a combination of intensity, phase and frequency characteristic of the electromagnetic waves measured. As an electric property of the measurable object, any one or a combination of electric field, dielectric constant, spatial gradient of electric field or dielectric constant, concentration, mass, size, shape, number of charges of charged particles that the measurable object possesses or interaction force with their surrounding medium can be measured of a change or changes thereof. As a magnetic property of the measurable object, magnetization due to electron spin or nuclear spin, or acousto-magnetic resonance due to electron spin or nuclear spin thereof can be measured. As an electromagnetic mechanical property of the measurable object, piezoelectric or magnetostriction property of the measurable object can be measured. Accordingly, measuring a change or changes in these property values in a living body, colloidal solution, liquid crystal, solid electrolyte, ionic crystal, semiconductor, dielectric, metal, magnetic material or magnetic fluid or a composite material thereof or a structure or a functional device composed of such a material is useful in clarifying the related phenomena. Especially, using the present invention in the determination of an active site in a brain makes it possible to identify an activated site at an extremely high position resolution.

DESCRIPTION OF REFERENCE CHARACTERS

Figure 1:
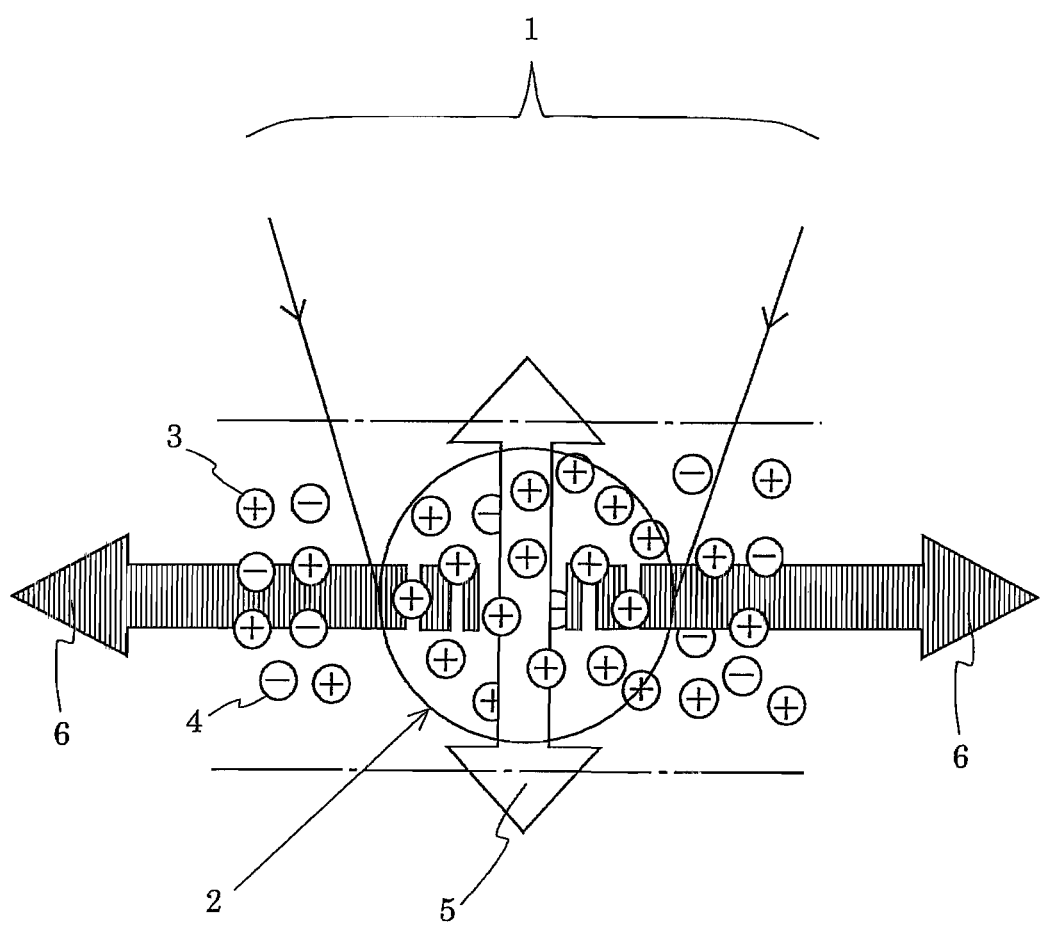
FIG. 1 is a diagram illustrating a state that a part of an object is irradiated with acoustic waves to induce electromagnetic waves.

1: acoustic beam
2: acoustic focused part
3: positive charged particle
4: negative charged particle
5: oscillating directions of acoustic waves
6: electromagnetic waves induced by acoustic waves
21: apparatus for property measurement with acoustically induced electromagnetic waves
22: anechoic chamber
23: measurable object
23a: acoustic focused part
24: retainer table
25: acoustic wave generator
26: acoustic waves
27: electromagnetic waves
28: antenna (array-type antenna or array-type coil)
28a: element antenna
29, 30, 50, 52, 60, 65, 75, 76:
   a control, measure and process unit
31: RF oscillator
31a: RF signal
31b: pulse signal
32: gate switch
33: pulse generator
34: amplifier
35: small signal amplifier
36: mixer
37: phase shifter
38: amplifier
39: low-pass filter
40: digital oscilloscope
41: personal computer
42, 62, 68, 78: signal line
43: time relaxation wave form of acoustically induced electromagnetic waves
51, 61, 77: lock-in amplifier
54: broadband acoustic wave pulse
55, 57: band-pass filter
66: gate pulse
67: spectrum analyzer
69: pulse for generating acoustic waves

BEST MODES FOR CARRYING OUT THE INVENTION

Explanation is given hereinafter of best modes for carrying out the present invention:

At the outset, mention is made of how electromagnetic waves are induced from an object when irradiated with acoustic waves.

FIG. 1 is a diagram illustrating a state that a part of an object is irradiated with acoustic waves to induce electromagnetic waves. In FIG. 1, an acoustic wave focusing beam 1 is shown as focused on a part 2 of a measurable object wherein positive charged particles 3 and negative charged particles 4 are shown by + and − signs, respectively, which are encircled with circles. Also, in the part 2 of the object, the positive charged particles 3 and the negative charged particles 4 lose their balance in concentration, exhibiting a charge distribution in which the positive charged particles 3 predominate. The arrow 5 indicates oscillating directions of acoustic waves whereas the arrow 6 indicates the electromagnetic waves produced with oscillations of the positive and negative charged particles 3 and 4 by acoustic waves and propagating in directions perpendicular to the arrow 5.

As shown in FIG. 1, where the positive and negative charged particles 3 and 4 when irradiated with the acoustic beam 1 are oscillated at a frequency of the acoustic waves in oscillating directions 5 of the acoustic waves, the oscillations which are of their charges induce the electromagnetic waves 6 which propagate in the directions perpendicular to the oscillating directions 5. By the way, when the positive and negative charged particles are oscillated identically, the electromagnetic waves then produced, respectively, by the positive and negative charged particles are deviated by $\pi$ in phase and canceled out by each other so that no electromagnetic waves may be produced as a whole. In the part 2 of the object, however, having a charge distribution in which the positive charged particles 3 are predominant so that there is no such cancellation, net electromagnetic waves 6 are induced.

Thus, observing acoustically induced electromagnetic waves to observe a change in intensity of the electromagnetic waves makes it possible to ascertain that a change has been brought about in charge distribution, namely that a change has occurred in concentration of positive charged particles 3 or negative charged particles 4 or both. To wit, from the measurement of acoustically induced electromagnetic waves it is possible to determine a change in a property value, here concentration, of charged particles in the object.

While in connection with FIG. 1 the measurement of acoustically induced electromagnetic waves is shown to determine a change in concentration of charge particles, the property value of charged particles whose change can be determined may be the mass, size, shape or number of charges of charged particles or interaction force with their surrounding medium as mentioned below.

Assuming that X: the position coordinate of a charge particle, M: the mass of the charged particle, S: the effective cross-sectional area on which the charged particle receives a force based on acoustic oscillations from its surrounding medium, p: the pressure of acoustic oscillations, ν: the frequency of the acoustic oscillations and t: time, the equation of motion of the charged particle can be expressed by equation (1) below.

$$M\frac{d^2 X}{dt^2} = Sp\sin 2\pi\nu t \qquad (1)$$

The solution of this equation can be expressed by expression (2) below.

$$X(t) = \frac{pS}{(2\pi v)^2 M} \sin 2\pi v t \quad (2)$$

The oscillation amplitude A of the charged particle can be expressed by equation (3) below.

$$A \equiv \frac{pS}{(2\pi v)^2 M} \quad (3)$$

From equation (3) above, it can be seen that the amplitude A of the charged particle varies with the mass of the charged particle. Also, since changing the size or shape of the charged particle changes the effective cross-sectional area S on which the charged particle receives the force due to the acoustic oscillations from its surrounding media, the amplitude A of the charged particle is changed also by a change in the size or shape. Further, since a change in interaction force with the medium surrounding the charged particle becomes a change in mass M approximately, it can be seen that a change in interaction force also causes a change in amplitude A of the charged particle.

Assuming that e is the charge of the charged particle, the oscillations of the charged particle can be expressed as the harmonic oscillations of charge e by P=eAsin2 π v t. The radiating power I(t) of electromagnetic waves radiating from the oscillation P in a unit time with the assumption that $\in_0$: vacuum dielectric constant and c: velocity of light can be expressed by equation (4) below.

$$I(t) = \frac{1}{6\pi \varepsilon_0 c^3} \left(\frac{d^2 P}{dt^2}\right)^2 \quad (4)$$

which if time averaged can yield equation (5) below.

$$I = \frac{1}{12\pi \varepsilon_0 c^3} [(2\pi v)^2 eA]^2 = \frac{4\pi^3 e^2}{3\varepsilon_0 c^3} v^4 A^2 \quad (5)$$

From equation (5) above, it can be seen that changing in amplitude A changes the radiating power of electromagnetic waves. Accordingly, from measurement of the acoustically induced electromagnetic waves it can be seen that the mass, size, shape or number of charges of charged particle or interaction force with its surrounding medium can also be determined. For instance, if it can be assumed from other information on the state of the measurable object or the knowledge gained by any other means that the concentration, mass, size, shape and number of charges are in the state that cannot be altered, a change in strength of electromagnetic waves measured can be tied to a change in interaction force with the medium surrounding the charged particle, for example to a change in polarizability of electrons or cations.

In the method of measuring a property of an object with the acoustically induced electromagnetic waves, the electric property that can be measured of the measurable object may be an electric field, a dielectric constant or a spatial gradient of electric field or dielectric constant.

Assuming that ρ: the density of charges which the measurable object 23 possesses, ρ can be related to the electric field according to the Poisson's equation (Gauss' law) as follows:

$$\rho = \nabla D = \nabla \in E = \nabla \in \cdot E + \in \cdot \nabla E \quad (6)$$

where D, $\in$ and E are the electric flux density, dielectric constant and electric field, respectively.

Since acoustically induced electromagnetic waves are caused by change of the charge density with time (∂ρ/∂t) information on the charge density, namely on the electric flux density gradient can be acquired from the intensity of electromagnetic waves. Further, in case the electric field can be assumed to be spatially constant, then ρ=∇∈·E, the spatial gradient of dielectric constant can be obtained. In case the dielectric constant can be assumed to be constant, information on the electric field gradient can likewise be acquired. In other words, electromagnetic radiation is microscopically created by charge oscillation by charges which a measurable object possesses. Macroscopically, it can be considered that electromagnetic waves are radiated by the electric flux density, dielectric constant or electric field changing with time. Accordingly, in measuring a function of a living body, e.g., its brain function for analysis as well in accordance with the method of the present invention, the acoustically induced electromagnetic waves have their root cause in change of intra-corporeal ion distribution with time and, with a sound focused area taken into account which is more macroscopic than the ion scale, can be regarded as a means for measuring a change in electric flux density or electric field gradient due to a neural activity.

In the method of measuring a property of an object with the acoustically induced electromagnetic waves, a magnetization due to electron spin or nuclear spin as the magnetic property of the measurable object can be measured as stated below. As with the electric polarization, an electromagnetic radiation is generated by a magnetization changing with time. According to the Maxwell's equation, a radiant electric field is proportional to the second derivative with respect to time of a magnetization (see Non-patent Reference 8). It follows, therefore, that the magnitude and direction of a magnetization can be determined from the strength or phase of electromagnetic waves.

In the method of measuring a property of an object with the acoustically induced electromagnetic waves, an acoustomagnetic resonance due to electron spin or nuclear spin as the magnetic property of the measurable object can be measured as stated below. From the fact that acoustic waves can efficiently be absorbed at a certain particular resonance frequency to change the direction of electron spin or nuclear spin, it is anticipated that the strength or phase of electromagnetic waves largely varies at that frequency. As the information, the resonance frequency can then be fixed upon. The rest can be to scan, as in ESR (electron spin resonance) or NMR (nuclear magnetic resonance), frequencies of sound waves to obtain a spectrum, thereby making it possible to obtain information on electron spin or nuclear spin. Also, the relaxation time of electron spin or nuclear spin can be measured.

In the method of measuring a property of an object with the acoustically induced electromagnetic waves, a piezoelectric or magnetostriction property as the electromagnetic mechanical property of the measurable object can be measured as stated below. An ionic crystal without inversion symmetry brings about an electric polarization according to its strain in principle. Thus, it is possible to derive the magnitude of a polarization from the intensity of acoustically induced electromagnetic waves. Scanning acoustic waves allows imaging a piezoelectric property of a measurable object. Further, it is possible to measure the piezoelectric tensor contactlessly without mounting an electrode on a measurable object from the direction of propagation of acoustic waves and the radiation distribution of electromagnetic waves. Since numerous bio-molecular crystals of bones or muscles in a living body have piezoelectric properties, their properties can be measured non-invasively. As for bones, there is a treatment which is said to heal a fracture sooner by irradiation with ultrasonic waves. There have been growing interest in researches on bones' piezoelectric properties. The method and apparatus of the present invention can provide a good application for piezoelectric properties of bio-specimens.

In the method of measuring a property of an object with the acoustically induced electromagnetic waves, a magnetostriction as the electromagnetic-magnetic property of the measurable object can be measured as stated below. The magnetostriction refers to a phenomenon that an electron orbit is altered by crystal strain to add a change to the electron spin magnetization through an orbit-spin interaction. Also, the crystal strain may bring about a change in crystal field splitting to alter the electron state, thereby altering the size of an electron spin magnetization. These changes with time are considered to generate electromagnetic waves. Therefore, it is possible to determine a relationship between the magnitude of magnetization, the orbit-spin interaction or the crystal strain and the sensitiveness of the electron orbit change or between the crystal field splitting and the strain sensitiveness or between the crystal field splitting and the electron spin state from the intensity of acoustically induced electromagnetic waves. It is possible to measure the magnetostriction tensor contactlessly and without mounting an electrode on the measurable object from the direction of propagation of acoustic waves and the intensity of radiation. The magnetostriction property can be imaged as can the piezoelectric property be.

According to the method of measuring a property of an object with acoustically induced electromagnetic waves, irradiating a measurable object with acoustic waves and measuring electromagnetic waves generated from the measurable object allow any one of properties of the object, including its electrical, magnetic and electromagnetic mechanical properties, to be determined from any one or a combination of strength, phase and frequency characteristics of the electromagnetic waves. Thus, the electric property can be determined of said measurable object, including a change or changes in one or more of property values for electric field, dielectric constant, spatial gradient of electric field and spatial gradient of dielectric constant and for concentration, mass, size, shape and number of charges of charged particles which the measurable object possesses and for interaction with a medium surrounding the charged particles. The magnetic property can be determined of said measurable object, including a property value for magnetization due to electron spin or nuclear spin in the measurable object or for acousto-magnetic resonance attributable to electron spin or nuclear spin in the measurable object. The electromagnetic mechanical property can be determined including a piezoelectric property or magnetostriction property of the measurable object.

An apparatus for measuring a property of an object with acoustically induced electromagnetic waves according to the present invention will be mentioned next.

Figure 2:
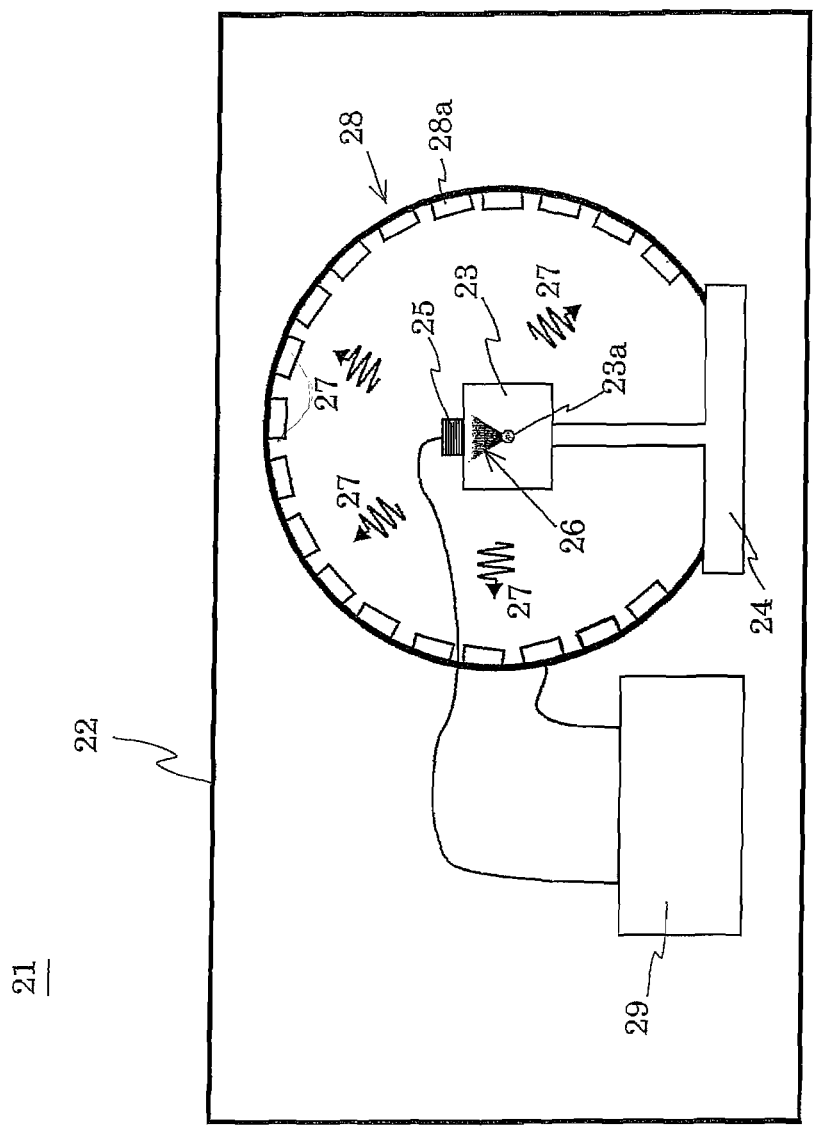
FIG. 2 is a diagram illustrating the structure of an apparatus for measuring a property of charged particles in an object by means of acoustically induced electromagnetic waves in accordance with the present invention.

FIG. 2 is a diagram illustrating the structure of an apparatus 21 for measuring a property of charged particles in an object by means of acoustically induced electromagnetic waves in accordance with the present invention. Using the Figure, an explanation is given of the structure and operation of the property measuring apparatus with the acoustically induced electromagnetic waves on the basis of charged particles which the object possesses.

The measuring apparatus 21 comprises an anechoic chamber 22, a retainer table 24 for holding thereon a measurable object 23 disposed in the anechoic chamber 22, an acoustic generator 25 disposed adjacent to or in contact with the object 23, an antenna 28 for receiving electromagnetic waves 27 generated from a region 23a on which acoustic waves 26 are focused that the acoustic generator 25 generates, and a control, measure and process unit 29 for controllably driving the acoustic generator 25 and measuring and processing electromagnetic wave signals 27 received by one or more of element antennas 28a of the antenna 28.

Here, the electromagnetic waves radiated from the measurable object 23 can be measured of their near field or non-near field, namely far field measurement. As will be described later, a magnetic field such as a near-field of the electromagnetic waves emitted from the measurable object 23 may be measured by SQUID. The antenna 28 may be an antenna of any type that is capable of detecting electromagnetic waves. For example, an antenna of every kind such as a loop antenna or array antenna or that made up of a looped or arrayed coil can be used.

To operate the measuring apparatus 21 of the present invention, the measurable object 23 is placed on the retainer table 24, acoustic waves are generated from the acoustic generator 25, and electromagnetic waves 27 radiated from the area 23a on which acoustic waves are focused are received by any one or more of the element antennas 28a of the array antenna or coil 28 for measurement at the control, measure and process unit 29. Also, scanning is effected over the area 23a where acoustic waves are focused and electromagnetic waves 27 are measured for each of the scanning positions to determine an intensity distribution of electromagnetic waves over a two-dimensional surface or a three-dimensional volume of the object.

While the element antennas 28a making up the array antenna 28 in FIG. 2 are shown disposed on a circumference in a cross section of the array antenna 8. The element antennas 28a are disposed at a uniform density thereof over 4 π radians around the object 23 so that they can receive electromagnetic waves induced from any desired part of the object or electromagnetic waves induced, if acoustic waves are focused, from any desired direction.

A way of and an apparatus for focusing acoustic waves on a desired position on a measurable object will be explained next.

Figure 3:
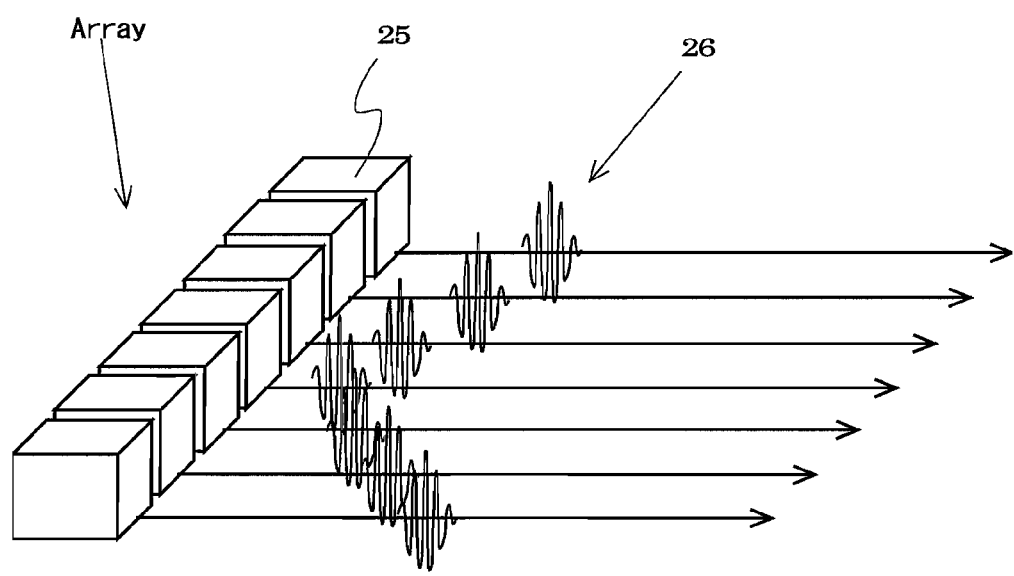
FIG. 3 is a diagram illustrating a way of focusing acoustic waves.

FIG. 3 shows a way of focusing acoustic waves. This way is called a phased array method. Acoustic wave pulses 26 generated individually by piezoelectric elements 25 arrayed in a row are focused by lagging and advancing acoustic wave pulses 26 in phase more than those from piezoelectric elements 25 lying towards the outside and inside of the row as shown. While the piezoelectric elements 25 are shown arrayed in a single row, they may be arrayed in a plurality of lines step by step so that acoustic wave pulses 26 generated by such piezoelectric elements 25 may, when shifted appropriately in phase, be focused over a three-dimensional volume of the measurable object.

Figure 4:
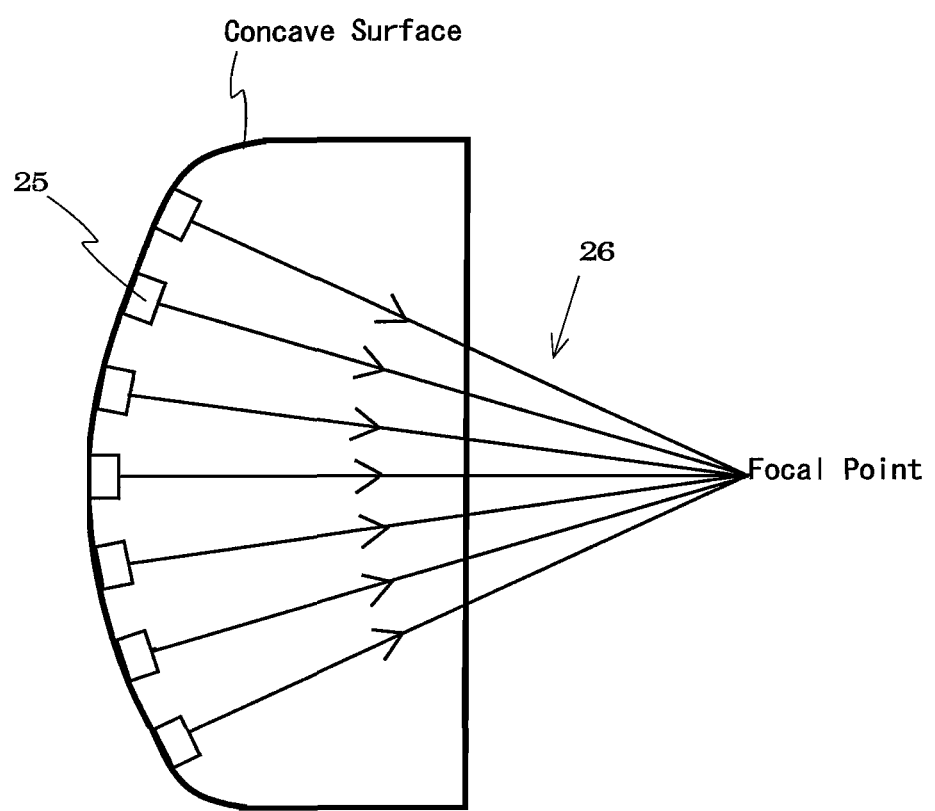
FIG. 4 is a diagram illustrating an alternative way of focusing acoustic waves.

FIG. 4 is a diagram illustrating an alternative way of focusing acoustic waves. This way is called an acoustic lens method. Piezoelectric elements 25 are disposed on a concaved surface with a curvature such that each point thereon has a normal focused on a focal point to generate acoustic wave pulses 26 simultaneously so that the individual acoustic wave pulses 26 propagate towards the focal point defined by the concaved surface and are thereby focused. By mechanically scanning the acoustic lens around a measurable object, it is possible to focus at a desired site over a three-dimensional volume of the measurable object. The two ways described above can also be combined.

Mention is made specifically of the measuring method and apparatus according to the present invention.

An explanation is first given of a first measuring method and apparatus according to the present invention.

Figure 5:
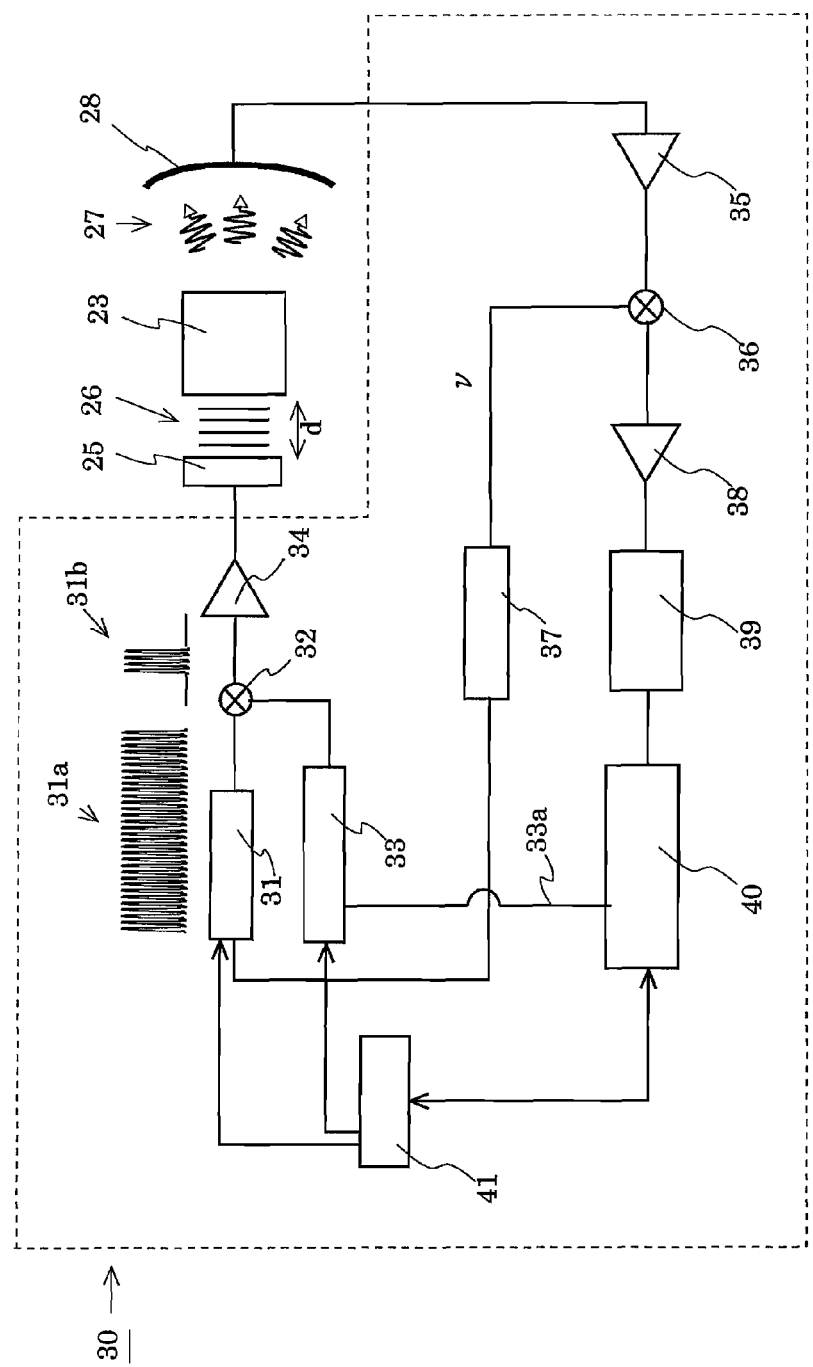
FIG. 5 is a block diagram illustrating the structure of a control, measure and process unit used in a first method of measurement according to the present invention.

FIG. 5 is a block diagram illustrating the structure of a control, measure and process unit used in the first measuring method of the present invention. Using the Figure, the structure and operation of the control, measure and process unit is described. The Figure shows the structure where acoustic waves for irradiation are narrow band pulses at a fixed frequency. In FIG. 5, the control, measure and process unit 30 is shown comprising an RF oscillator 31, a gate switch 32 for shaping an RF signal 31a output from the RF oscillator 31 into a pulsed signal 31b of fixed shape, a pulse generator 33 for turning the gate switch 32 on and off and an amplifier 34 for amplifying the pulsed signal 31b output from the gate switch 32 and feeding the pulsed signal 31b output from the amplifier 34 into the acoustic generator 25 for generating acoustic wave pulses 26.

The control, measure and process unit 30 also comprises a small signal amplifier 35 connected to the array antenna 28 for amplifying electromagnetic waves received by the array antenna 28, a mixer 36 for phase-detecting the electromagnetic waves from the small signal amplifier 35 with an oscillation frequency ν of the RF oscillator 31, a phase shifter 37 for controlling the phase of an oscillation frequency ν signal of the RF oscillator 31 to furnish therewith and control the mixer 36, an amplifier 38 for amplifying an electromagnetic wave signal passed through the mixer 36, a low-pass filter 39 for passing frequency components lower than at a fixed frequency selectively of the electromagnetic wave signal amplified by the amplifier 38, and a digital oscilloscope 40 for measuring the intensity of the electromagnetic wave signal passed through the low-pass filter 39 in synchronism with pulse generation timings produced by the pulse generator 33. Also, indicated by 33a is a signal line for synchronizing the pulse generator 33 and the digital oscilloscope 40.

The control, measure and process unit 30 also includes a personal computer 41. The RF oscillator 31, the pulse generator 33 and the digital oscilloscope 40 are connected to the personal computer 41. The personal computer 41 is used to control the RF signal 31a and the pulsed signal 31b, to acquire an electromagnetic wave signal measured by the digital oscilloscope 40 and to control measurement by the digital oscilloscope 40.

While in the description above the phase detection is shown as effected with the frequency of acoustic waves, it may be effected with the frequency of acoustic wave pulses in which case the phase phase shifter 37 may be connected to the pulse generator 33 to use the oscillation frequency of the pulse generator 33 as a reference signal.

While in the Figure the structure of a controller is shown in which only one acoustic generator is driven, where a desired site of the object is to have acoustic wave pulses focused thereon and to be scanned in position as described above, a plurality of acoustic generators as shown should be provided together with a plurality of controllers as shown whereby they are controllably driven. Using the phase detection which can exclude external noises contained in the other frequency components permits detecting even an extremely small change in intensity of electromagnetic waves. Also, with the phase detection which allows the phase of the reference signal to be varied with the phase shifter 37 and measured, it is possible to find which of positive or negative charged particles in oscillation the electromagnetic waves for measurement are based on according to the positive or negative sign of a measured value taken when the electromagnetic waves and the reference signal are matched in phase.

Figure 6:
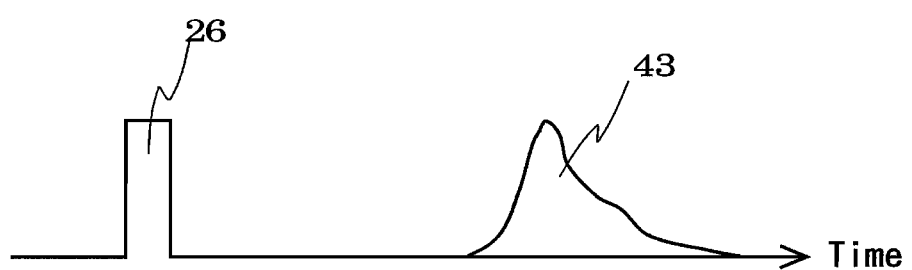
FIG. 6 is a diagram illustrating a method of measuring a change with time characteristic of a property value of charged particles in accordance with the present invention.

Also, by selecting the distance d between the acoustic generator 25 and the site of the object 23 to be irradiated with acoustic wave pulses to adjust the time period it takes an acoustic wave pulse to propagate over the distance d to be longer than the time duration of an acoustic wave pulse or adjusting the duration of the acoustic wave pulse to be shorter than that propagation time period, it is possible to ensure that the acoustically induced electromagnetic wave signal radiated from the object can be measured upon separation in time from electromagnetic noises produced when the acoustic generator 25 generates acoustic wave pulses. In this case, as shown in FIG. 6, it is possible to measure a time dependent change in property value of charged particles contained in the object by measuring variations with time of the intensity of electromagnetic waves 43 detected subsequent to irradiation with an acoustic wave pulse 26. For example, a relaxation time by acoustic excitation of property value of the charged particles can be measured.

Mention is next made of a second measuring method and apparatus according to the present invention.

Figure 7:
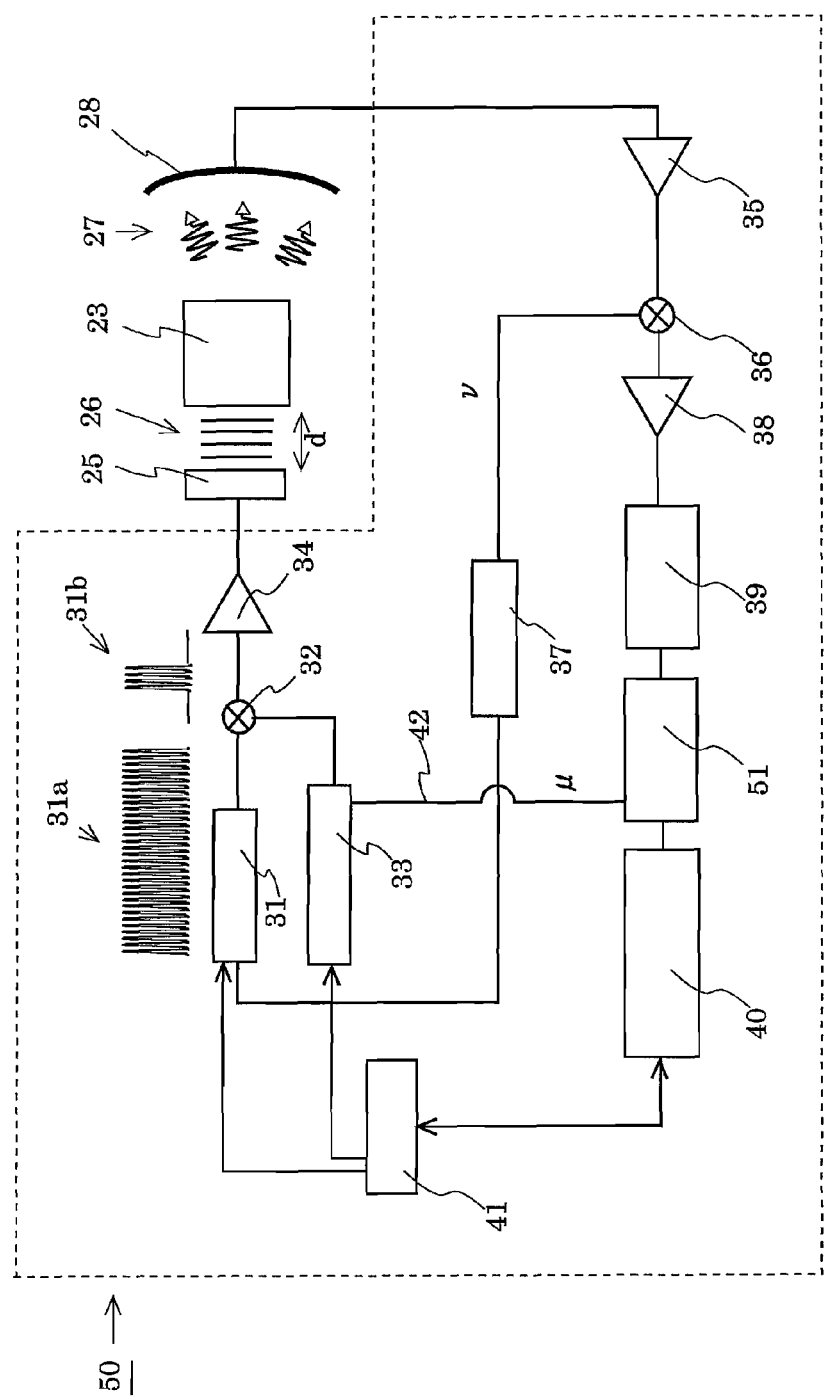
FIG. 7 is a block diagram illustrating the structure of a control, measure and process unit used in a second method of measurement according to the present invention.

FIG. 7 is a block diagram illustrating the structure of a control, measure and process unit used in the second measuring method according to the present invention. The control, measure and process unit 50 differs from that in the structure shown in FIG. 1 that a lock-in amplifier 51 is disposed between the low-pass filter 39 and the digital oscilloscope 40. The lock-in amplifier 51 is used to detect, by locking-in, an electromagnetic wave signal passed through the low-pass filter 39 with the oscillation frequency μ of the pulse generator 33 used as a reference signal. Indicated by 42 is a signal line for supplying the lock-in amplifier 51 with the oscillation frequency μ of the pulse generator 33.

According to this method in which both the frequency ν of acoustic waves and the pulse period 1/μ of acoustic wave pulses are used for phase detection, it is possible to further exclude external noises having the other frequency components and to detect even an extremely small change in intensity of electromagnetic waves.

Here, the lock-in amplifier comprises a gate switch and a narrowband amplifier for phase detection used for measurement based on the same measuring principles as those of phase detection. A lock-in amplifier has been marketed having a set of gate switch and narrowband amplifier for applications where the reference frequency for phase detection is low. Since the phase detection where the reference frequency is low is customarily called lock-in detection, the terms "lock-in amplifier" and "lock-in detection" are used here if the reference frequency for phase detection low.

Mention is next made of a third measuring method and apparatus according to the present invention.

In a brain or muscle tissue of a living body, acoustic waves whose frequency is higher damp quickly and those of lower frequency reach deep. Consequently, measuring the frequency of electromagnetic waves acoustically induced makes it possible to find if their emission source is deep or shallow. This phenomenon is utilized in the third method of the present invention. This method can be found from the frequency determined of electromagnetic waves if their emission source is deep or shallow to enhance its position resolution depthwise in an acoustic wave focused part.

Figure 8:
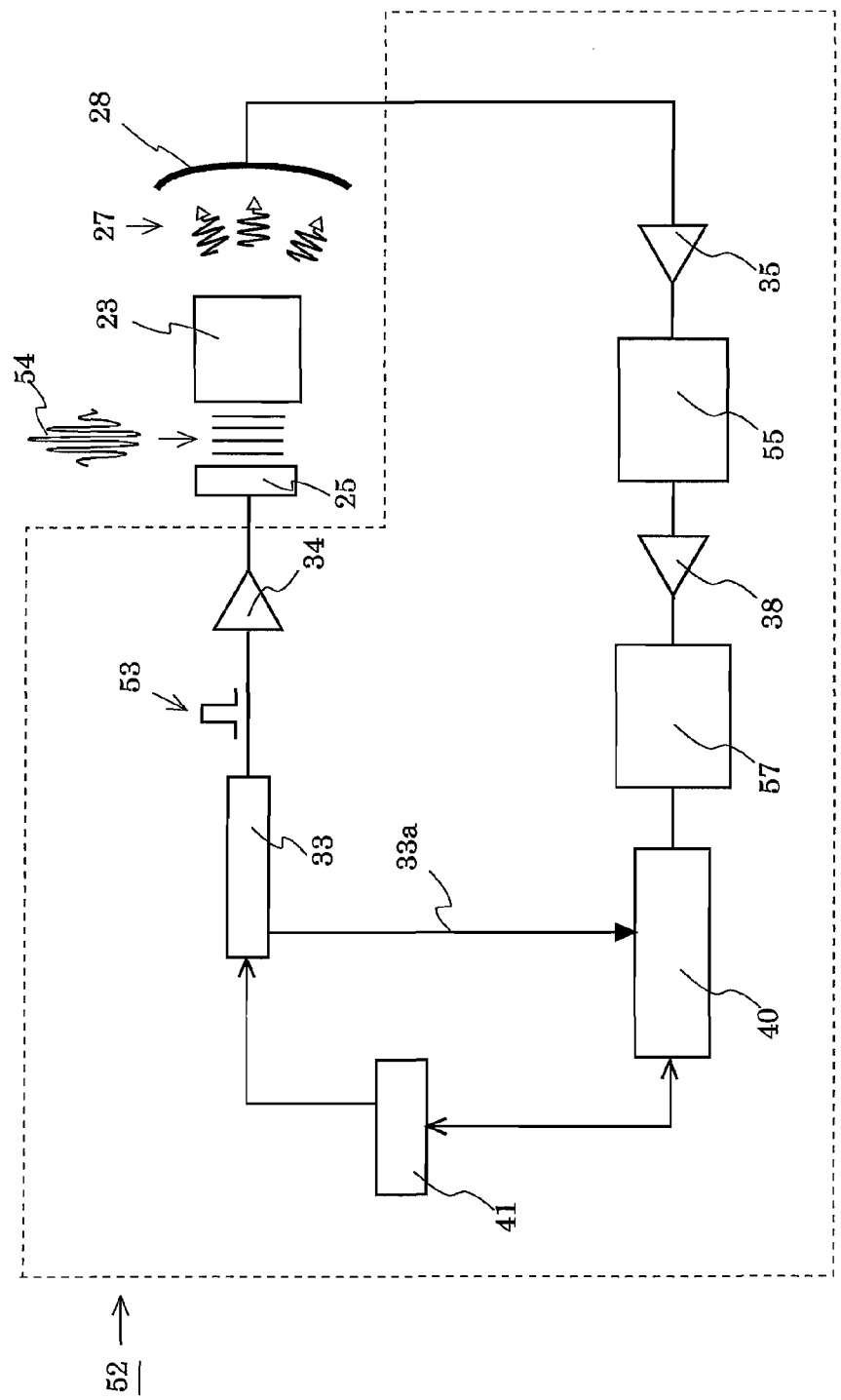
FIG. 8 is a block diagram illustrating the structure of a control, measure and process unit used in a third method of measurement according to the present invention.

FIG. 8 is a block diagram illustrating the structure of a control, measure and process unit used in a third measuring method of the present invention. The control, measure and process unit 52 is devoid of the RF oscillator 31 in the structure of FIG. 1 and is configured so that a single pulse 53 generated from the pulse generator 33 is applied to the acoustic generator 25. The acoustic generator 25 may comprise, e.g., a piezoelectric element. When the single pulse 53 is applied to the piezoelectric element, the piezoelectric element will oscillate freely until its oscillation energy is dissipated to become zero. Acoustic wave pulse 54 by the free oscillations of the piezoelectric element is a wideband acoustic wave pulse in which frequencies are distributed over a wider range than with the narrowband acoustic wave pulse 31b in FIG. 1.

The control, measure and process unit 52 as shown has its measuring section comprising a first bandpass filter 55 for passing particular frequency components in an electromagnetic wave signal amplified by the small signal amplifier 35, the narrowband amplifier 38 for amplifying the frequency components transmitted through the first bandpass filter 55, a second bandpass filter 57 for passing particular frequency components in the frequency components amplified by the narrowband amplifier 38 and the digital oscilloscope 40 for integrating the frequency components passed through the second bandpass filter 57 to measure the intensity of electromagnetic waves.

In measurement using the control, measure and process unit 52, frequency components of an electromagnetic wave signal are roughly chosen through the first bandpass filter 55, of which frequency components are finely selected through the second bandpass filter 57. Intensities of the selected frequency components are measured of the electromagnetic wave signal to identify the frequency of the electromagnetic waves from the frequency exhibiting the maximum intensity. The depth-wise position can be determined in the acoustic wave focused part from a frequency of the measured electromagnetic waves.

According to this method, since acoustic waves higher in frequency quickly attenuate and acoustic waves lower in frequency reach deeper in a brain or muscle tissue of a living body, it is possible to know a depthwise position of the acoustic waves in their focused part from a frequency of the measured electromagnetic waves.

Mention is next made of a fourth measuring method and apparatus according to the present invention.

Figure 9:
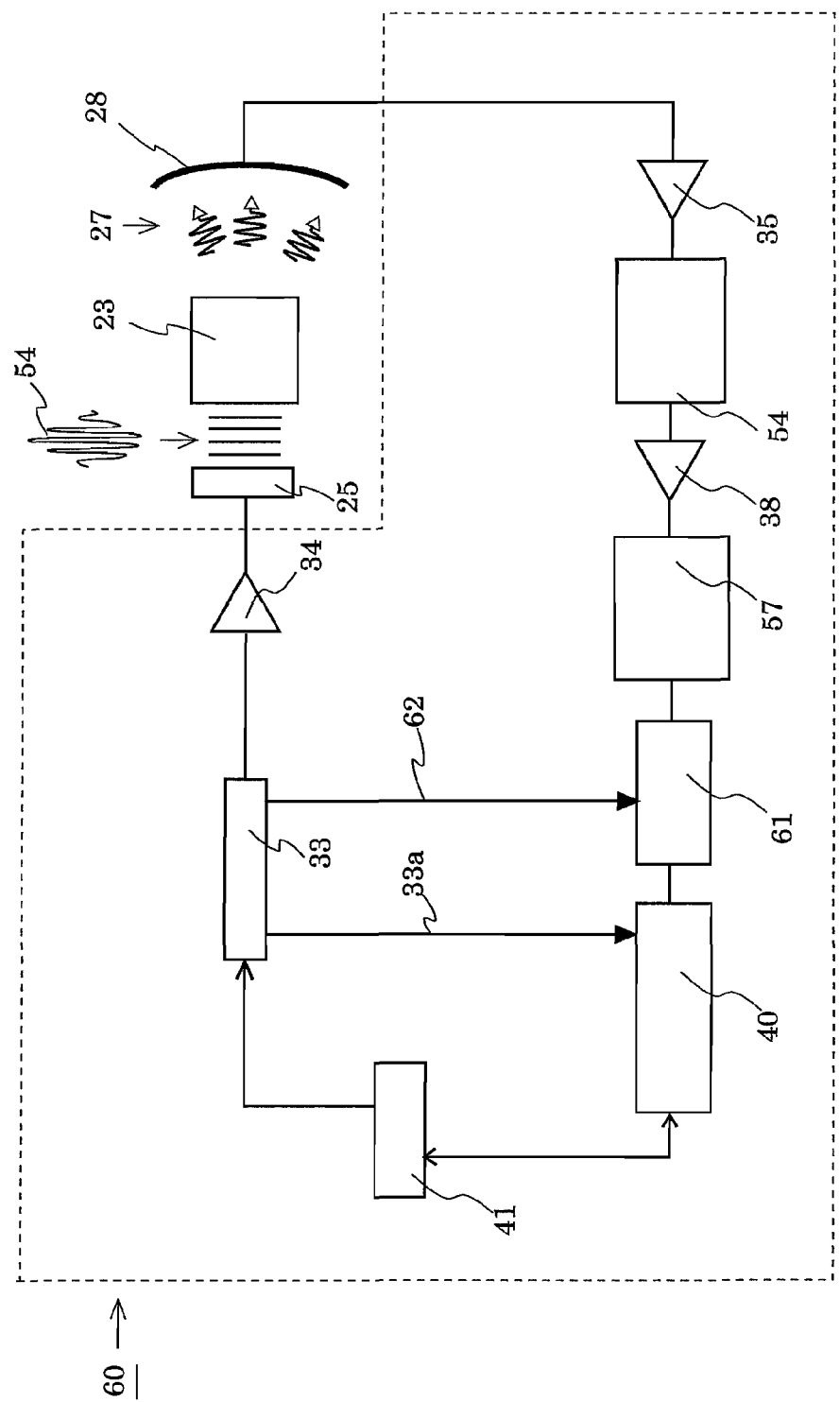
FIG. 9 is a block diagram illustrating the structure of a control, measure and process unit used in a fourth method of measurement according to the present invention.

FIG. 9 is a block diagram illustrating the structure of a control, measure and process unit 60 used in a fourth measuring method of the present invention. The control, measure and process unit 60 has its measuring section which differs from that in the structure shown in FIG. 8 only in that between the second bandpass filter 57 and the digital oscilloscope 40 its control section includes a lock-in amplifier 61 that uses pulse generation timings of the pulse generator 33 as a reference frequency. Indicated at 62 is a signal line for supplying the lock-in amplifier 61 with pulse generation timings of the pulse generator 33 as a reference frequency.

In the third method, the intensity of electromagnetic waves is measured by integrating electromagnetic wave signals by means of the digital oscilloscope. This method integrates electromagnetic wave signals excluded of external noises by the lock-in amplifier 61 so that it can exclude external signals having other frequency components as well to enable a further smaller change in intensity of electromagnetic waves than with the third method to be detected.

Mention is next made of a fifth measuring method and apparatus according to the present invention.

Figure 10:
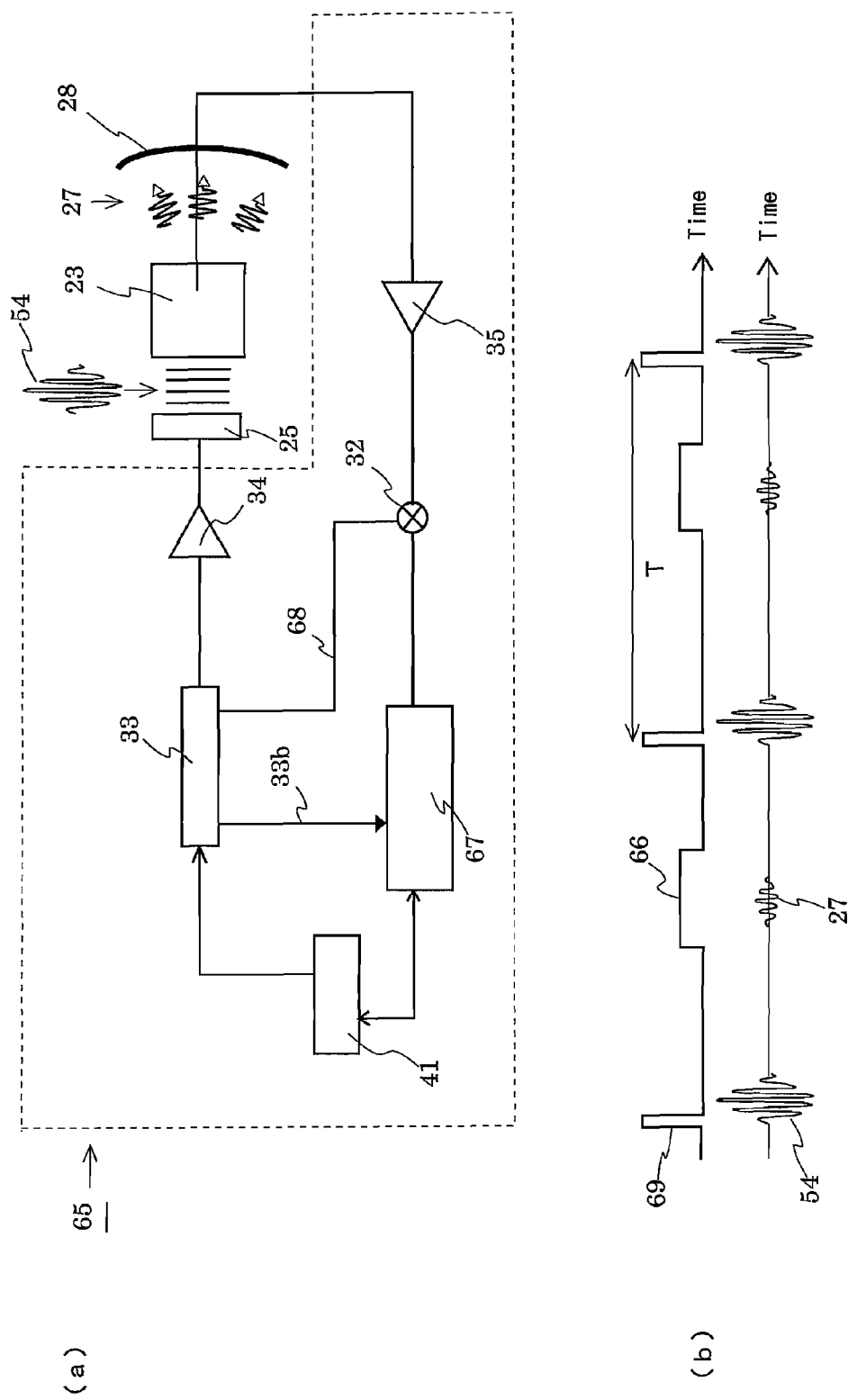
FIG. 10 illustrates a block diagram of the structure of a control, measure and process unit used in a fifth method of measurement according to the present invention wherein (a) shows the apparatus structure and (b) shows occurrence timings of gate pulses and acoustic generating pulses produced by a pulse generator, those of acoustic waves generated by an acoustic generator and those of electromagnetic waves induced in an object.

FIG. 10 is a block diagram illustrating the structure of a control, measure and process unit used in a fifth measuring method of the present invention, showing the apparatus structure at (a). At (b) there are shown generation timings of gate pulses 66 and acoustic generating pulses 69 produced by the pulse generator 33, those of acoustic waves 54 generated by the acoustic generator 25 and those of electromagnetic waves 27 induced in an object.

The control, measure and process unit 65 as shown in FIG. 10(a) has its measuring section comprising a small signal amplifier 35 for amplifying received electromagnetic waves 27, the gate switch 32 by which an electromagnetic wave signal amplified by the small signal amplifier 35 is passed for a duration of the gate pulse 66 produced by the pulse generator 33 and a spectrum analyzer 67 for displaying with a frequency signal the electromagnetic wave signal passed the gate switch 32. The spectrum analyzer 67 has a function to detect and memorize the signal intensity for each of frequency components. The function of the spectrum analyzer 67 can be processed by Fourier transformation at a processor equipped in the control, measure and process unit 65. A signal line 68 is provided to supply the gate switch 32 with gate pulses 66 and a signal line 33b is provided to synchronize the pulse generator in operation with the spectrum analyzer 67.

As can be seen from the upper waveform chart in FIG. 10(b), a gate pulse 66 occurs in a time interval between two successive acoustic wave generating pulses 69. The lower waveform chart shows a timing of generation of an acoustic wave pulse 54 produced at the acoustic generator 25 by an acoustic wave generating pulse 69 and a timing of generation of electromagnetic waves 27 induced upon arrival of the acoustic wave pulse 54 at the object 23. As shown, the gate pulse 66 and electromagnetic waves 27 are made coincident in timing of generation. And, signals introduced into the spectrum analyzer 67 are only in time intervals in which electromagnetic waves 27 are induced, thereby excluding external noises in the other time intervals and making it possible to detect a change extremely small in intensity of electromagnetic waves.

Mention is next made of a method of and an apparatus for determining a polarity of charges of a source of emission of electromagnetic waves in the case of using broadband acoustic wave pulses.

Figure 11:
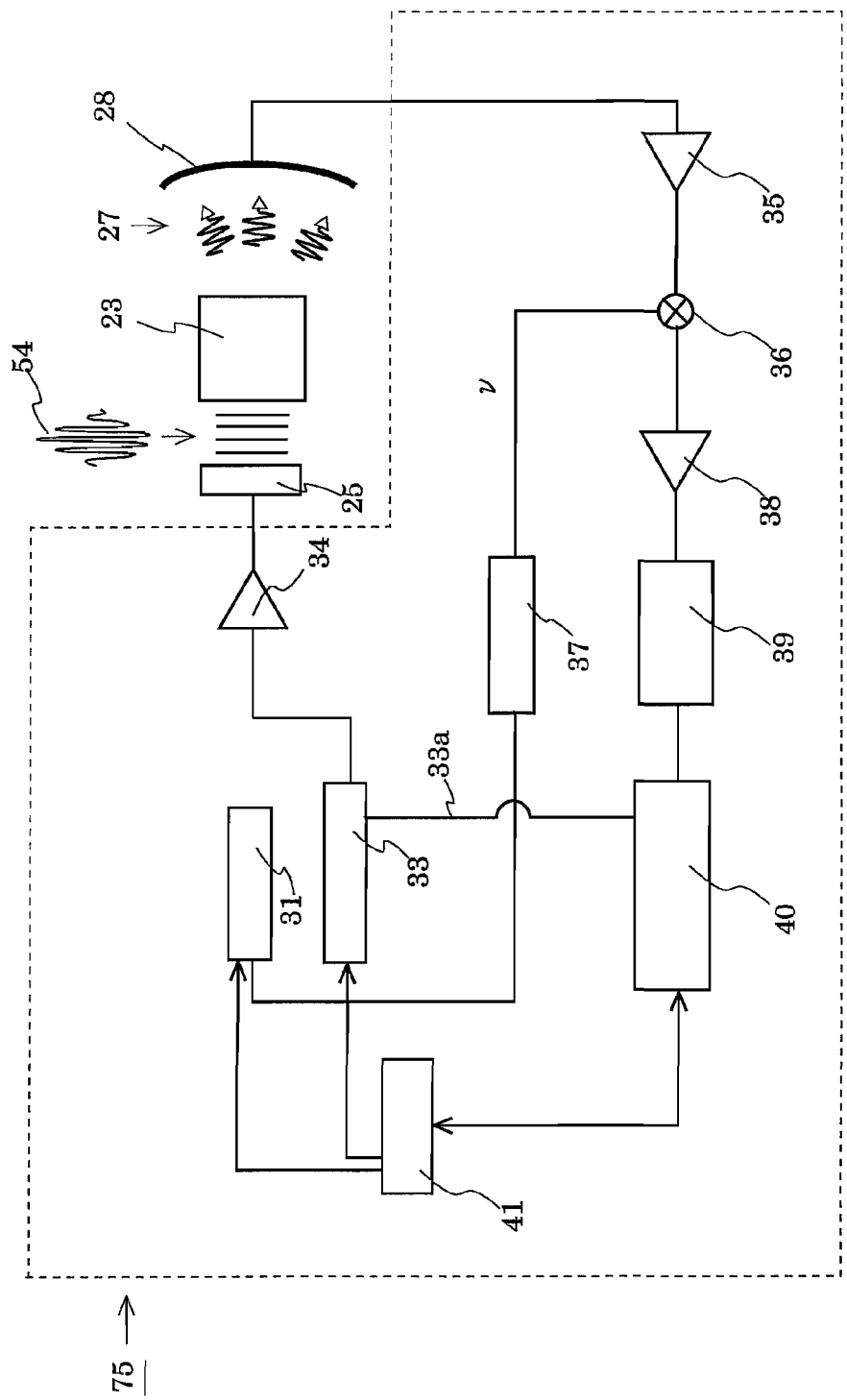
FIG. 11 is a block diagram illustrating the structure of a control, measure and process unit used in determining a polarity of charges of a source of emission of electromagnetic waves in the case of using broadband acoustic wave pulses.

FIG. 11 is a block diagram illustrating the structure of a control, measure and process unit 75 used in determining a polarity of charges of a source of emission of electromagnetic waves in the case of using broadband acoustic wave pulses. The control, measure and process unit 75 has its measuring section comprising the small signal amplifier 35 that amplifies received electromagnetic waves, the mixer 36 by which the electromagnetic waves amplified at the small signal amplifier 35 are phase-detected with an oscillation frequency ν of the RF oscillator 31, a phase shifter 37 for controlling the phase of an oscillation frequency ν of the RF oscillator 31 for supply to control operation of the mixer 36, the amplifier 38 that amplifies an electromagnetic wave signal passed through the mixer 36, the low pass filter 39 that passes only components of frequencies less than a certain frequency among the electromagnetic signal amplified by the amplifier 38, and the digital oscilloscope 40 for measuring the intensity of an electromagnetic wave signal passed through the low pass filter 39.

Thus, in measurement, the reference signal is varied in phase by the phase shifter 37 until it is matched in phase with the electromagnetic wave signal; then finding if the measured value is positive or negative makes it possible to determine that the electromagnetic waves measured are based by the oscillations of positive charged particles or of negative charged particles.

Figure 12:
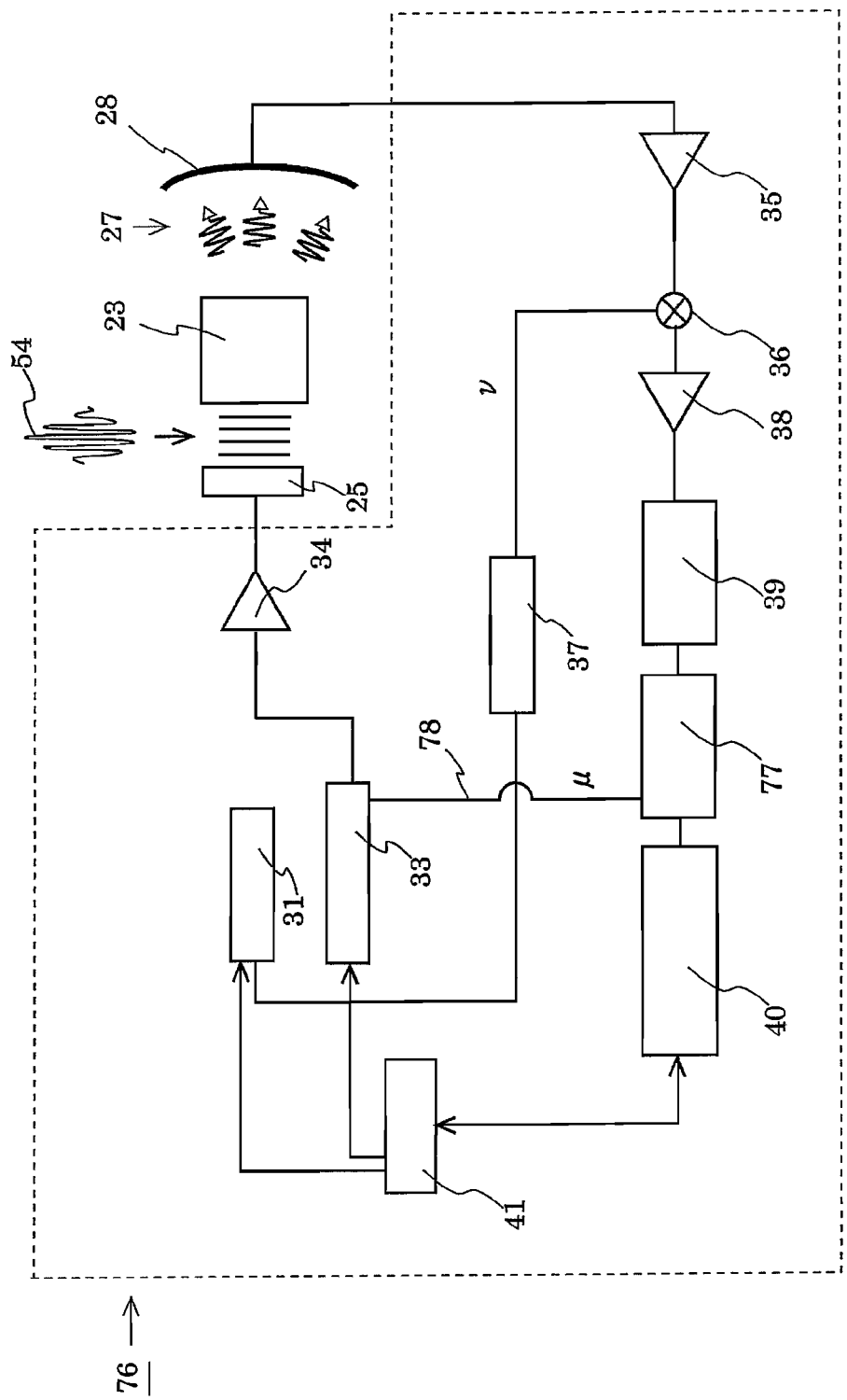
FIG. 12 is a block diagram illustrating the structure of another control, measure and process unit used in determining a polarity of charges of a source of emission of electromagnetic waves in the case of using broadband acoustic wave pulses.

FIG. 12 is a block diagram illustrating the structure of another control, measure and process unit 76 used in determining a polarity of charges of a source of emission of electromagnetic waves in the case of using broadband acoustic wave pulses. The control, measure and process unit 76 has its measuring section which is the same in structure as that in FIG. 11 except that a lock-in amplifier 77, in which reference signal is supplied from the oscillation frequency of the pulse generator 33, is included between the low pass filter 39 and the digital oscilloscope 40. 78 is a signal line to supply the oscillation frequency of the pulse generator 33 to the lock-in amplifier 77. Since this method compared with that of FIG. 11 can exclude external noises having other frequency components, this method is able to determine the charge polarity if the electromagnetic waves are extremely small in intensity.

In the apparatus for measuring properties of an object with acoustically induced electromagnetic waves in accordance with the present invention, a magnetic field of electromagnetic waves from the measurable object 23 can be measured using a SQUID (superconducting quantum interference device). The SQUID is a device having one or two Josephson junctions in a ring formed of a superconductor. With one Josephson junction and with two Josephson junctions, it is referred to as RF-SQUID and DC-SQUID, respectively. The SQUID is a supersensitive magnetic sensor having a quantization phenomenon of superconductor and has a sensitivity more than hundred times compared with the conventional sensor. The SQUID is capable of detecting a feeble electric field as weak as one fifty-millionth of earth magnetism.

The control, measure and process unit 29, 30, 50, 52, 60, 65, 75, 76 mentioned above can be made up having a computer, a display and a memory. If a given time of a time sequence signal of acoustically induced electromagnetic waves is Fourier-transformed in an algorithm of the fast Fourier transformation (FFT) by the computer, the time of computation can then be shortened. Means for obtaining a Fourier spectrum to this end can be a DSP (digital signal processor) or FFT unit which is exclusive or dedicated without recourse to a computer. Also, while as regards the signal processing such as amplifying and demodulating, individual circuit components and means for measuring frequencies have been shown variously, they can be substituted by an integrated circuit tailored for the receiver or DSP.

In the present method of measuring an object's property with acoustically induced electromagnetic waves, the magnetostriction property as an electromagnetic-magnetic property of the measurable object can be measured as stated below.

The magnetostriction is meant a phenomenon that crystal strain alters an electron orbit so that a change in spin magnetization is added through the orbit-spin interaction. Or, the crystal strain may cause a change in crystal field splitting which changes the electron state, thereby changing the magnitude of electron spin magnetization. A change in these with time is thought to generate electromagnetic waves. Accordingly, from the intensity of acoustically induced electromagnetic waves, it is possible to determine the magnitude of magnetization, the orbit-spin interaction or the relationship between the crystal strain and the sensitiveness of electron orbit change, between the crystal field splitting and the sensitiveness of strain or between the crystal field splitting and the electron spin state. From the acoustic propagation bearing and radiant intensity, it is possible to measure the magnetostriction tensor contactlessly or without an electrode mounted on the measurable object. As is the piezoelectric property, the magnetostriction property can be imaged.

According to a method of measuring a property of an object by acoustically induced electromagnetic waves, upon irradiating the measurable object with acoustic waves and measuring electromagnetic waves generated from the measurable object, it is possible to determine any of electric, magnetic and electromagnetic mechanical properties from any one or a combination of the intensity, phase and frequency characteristic of the electromagnetic waves.

Thus, as electric property of the measurable object, any one of electric field, dielectric constant, spatial gradient of electric field or dielectric constant, concentration, mass, size, shape and number of charges of charged particles that the measurable object possesses and interaction with their surrounding medium or a change or changes in one or more of these property values can be measured. As a magnetic property of the measurable object, magnetization due to electron spin or nuclear spin, or acousto-magnetic resonance due to electron spin or nuclear spin of the measurable object can be measured. As an electromagnetic mechanical property of the measurable object, piezoelectric or magnetostriction property of the measurable object can be measured.

Mention is next made supplementarily of the case that the method and apparatus of the present invention for measuring a property of an object is applied to identifying an active site in a brain.

The operating frequencies of piezoelectric element currently used for medical care are 3.5 MHz, 5 MHz, 7.5 MHz, 10 MHz and 30 MHz. Assuming that acoustic waves travel in a human body at a velocity of 1600 m/second, acoustic waves of 7.5 MHz come to have a wavelength of 213 μm in a human body and, if used for a human body, can become focused on a region of about 213 μm. It follows, therefore, that if the method of the present invention is applied to identifying an active site in a human brain using acoustic waves of frequency 7.5 MHz, it is then possible to identify the active site in the brain at a resolution of 213 μm. The use of high-frequency acoustic waves of 100 MHz or more for the purpose of dealing with other than human bodies makes a resolution of 10 μm or less possible.

Focusing acoustic waves has practically been applied in ways as shown in FIGS. 3 and 4 to the medical field, e.g., used in a modern therapy without need for a surgical operation, such as extracorporeal shock wave lithotripsy (see Non-patent Reference 6) or treatment by high intensity focused ultrasound (see Non-patent Reference 7) used for cancer therapy. As for a brain, it is preferred to irradiate acoustic waves via an acoustic matching layer on the cranial bones which is less transmissive of acoustic waves. In so identifying an active area in a brain, the apparatus of the present invention for measuring an object's property with acoustically induced electromagnetic waves can be used for measurement. In this case, the measured data of brain's acoustically induced electromagnetic waves are separately taken and the recorded data can be analyzed by a computer.

Example 1

The present invention in further detail with reference to specific examples will be mentioned.

Figure 13:
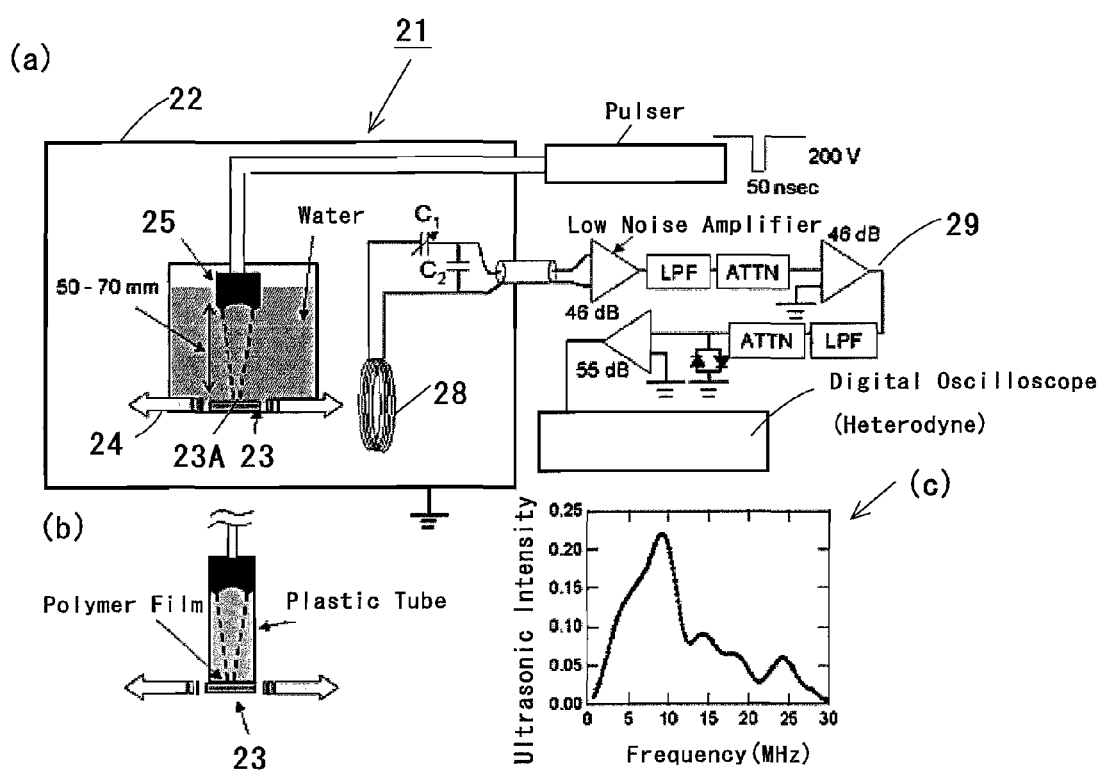
FIG. 13 diagrammatically illustrates the structure of an apparatus for measuring a property of an object with acoustically induced electromagnetic waves in Example 1, showing at (a) the apparatus structure, at (b) a modification of ultrasonic probe and at (c) a waveform of ultrasonic waves, respectively.

FIG. 13 diagrammatically illustrates the structure of an apparatus measuring a property of an object with acoustically induced electromagnetic waves in Example 1, showing at (a) the apparatus structure, at (b) a modification of ultrasonic probe and at (c) a waveform of ultrasonic waves, respectively.

As shown in FIG. 13(a), the measuring apparatus 21 comprises the anechoic chamber 22, the retainer table for holding thereon a measurable object 23 disposed in the anechoic chamber 22, the acoustic generator 25 disposed adjacent to or in contact with the object 23, a loop antenna 28 for receiving electromagnetic waves generated from a region 23a on which acoustic waves 26 are focused that the acoustic generator 25 generates, and the control, measure and process unit 29 (not shown) for controllably driving the acoustic generator and measuring and processing electromagnetic wave signals 27 received by the loop antennas 28. The acoustic generator 25 comprises a pulser (Panametrics Inc., model 5077PR) and an ultrasonic vibrator of polyvinylidene fluoride driven by this pulser. The pulser produced a rectangular wave of 50 ns pulse width at a repetition frequency of 100 to 500 Hz (see FIG. 13(c)). The ultrasonic vibrator was spaced from the measurable object 23 at a distance of 50 to 70 mm across a water medium used. The acoustic waves traveling in water at a velocity of 1500 m/s, it turned out that electromagnetic waves ultrasonically generated from the measurable object 23 occurred every 33 to 47 μs. The measurement by a broadband underwater microphone indicated that the ultrasonic waves were focused on an area of 2 mm diameter at a position of the measurable object 23.

At the output side of the loop antenna 28, there are a pair of tuning capacitors of variable capacitance whose output is input into a small signal amplifier via a line of coaxial cable or the like. As shown, the small signal amplifier is connected in turn to a first small signal amplifier having a voltage gain of 46 dB, a low pass filter, an attenuator, a second small signal amplifier having a voltage gain of 46 dB, an attenuator, a diode limiter and a third small signal amplifier having a voltage gain of 55 dB. The output of the third small signal amplifier is input to the digital oscilloscope.

Example 2

An apparatus for measuring a property of charged particles was prepared which was identical to that in Example 1 except that the output of the third small amplifier was heterodyne-detected. The mixer used was a double balanced mixer.

Example 3

Using a semiconductor made of GaAs crystal as the measurable object 23, acoustically induced electromagnetic waves were detected with the apparatus of Example 1 or 2 for measuring a property of charged particles.

Figure 14:
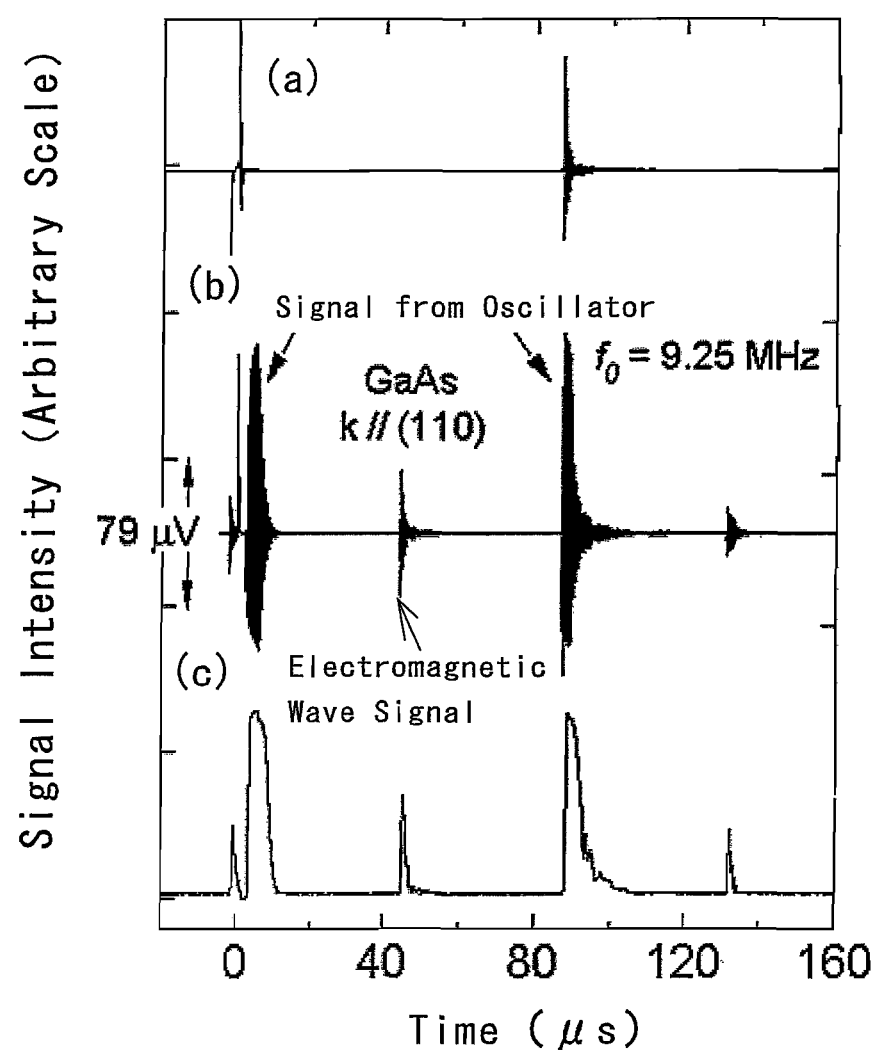
FIG. 14 illustrates detected waveforms of acoustically induced electromagnetic waves from semiconductor GaAs crystal as the object, showing at (a) an ultrasonic waveform, at (b) a waveform obtained in the property measuring apparatus in Example 1 and at (c) a waveform obtained in a property measuring apparatus in Example 2.

FIG. 14 illustrates detected waveforms of acoustically induced electromagnetic waves from semiconductor GaAs crystal as the object 23, showing at (a) an ultrasonic waveform, at (b) a waveform obtained in the property measuring apparatus in Example 1 and at (c) a waveform obtained in a property measuring apparatus in Example 2. In the graph of FIG. 14, the abscissa axis represents time (in μs) and the ordinate axis represents the signal intensity (in arbitrary scale). The GaAs used was a non-doped crystal of 350 μm thickness. Its [110] axis was aligned in orientation with the direction of wave number vector k of the incident ultrasonic waves. The GaAs is a material whose piezoelectric coefficient is expressed by equation (7) below.

$$|d_{14}^{GaAs}|=2.7 pC/N \qquad (7)$$

Accordingly, if the wave number vector of longitudinal acoustic mode of the GaAs is parallel to piezoelectric axis <110>, it is predicted that electromagnetic waves are generated.

FIG. 14(a) shows an ordinary ultrasonic echo signal. It is seen that excitation (0 μs) by a high-frequency pulse of about 9.25 MHz produces an ultrasonic echo with a delay of 88 μs.

As is apparent from FIG. 14(b), an electromagnetic wave signal is seen to occur at 44 μs that is one half of the period, namely at an instant when GaAs is irradiated with ultrasonic waves. This measurement was performed with the charged particles' property measuring apparatus of Example 1, where the small signal amplifier had an amplification degree of 82 dB and the digital oscilloscope had an integration of 200 pulses (in 1 second). The electromagnetic waves obtained from the GaAs had an peak to-peak signal intensity (Vp-p) of 68 μV.

As is apparent from FIG. 14(c), an electromagnetic wave signal is seen to occur at 44 μs that is one half of the period, at an instant when GaAs is irradiated with ultrasonic waves. This measurement was performed with the charged particles' property measuring apparatus of Example 2 using the heterodyne detection and gave rise to an electromagnetic wave signal more lucid than that shown in FIG. 14(c).

Figure 15:
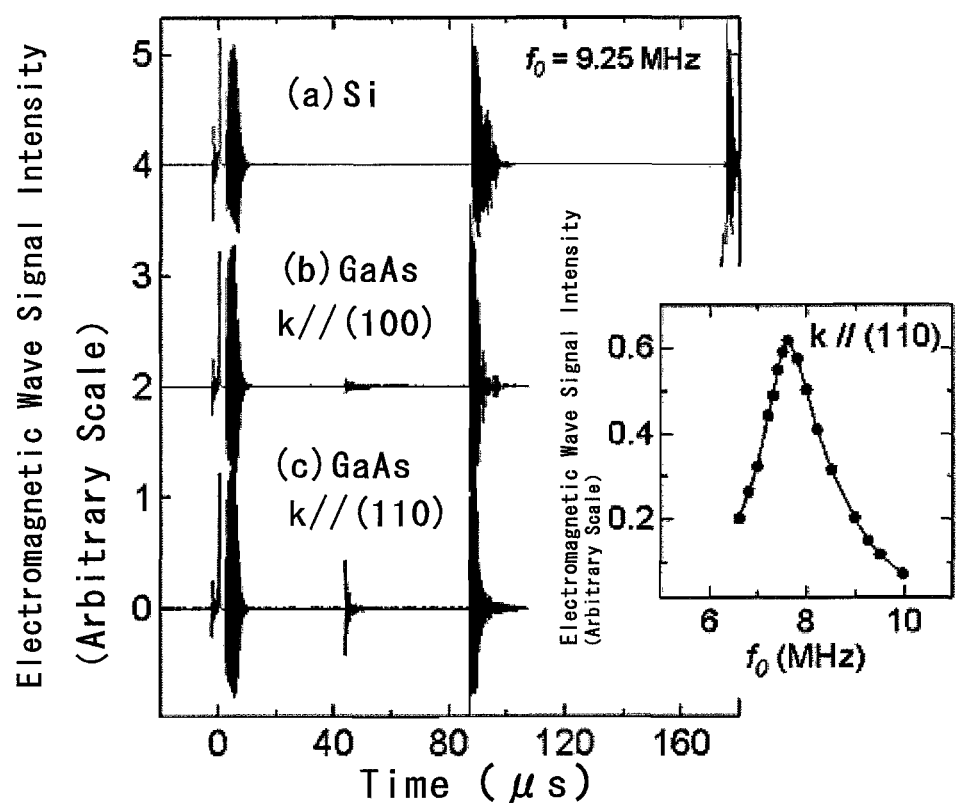
FIG. 15 illustrates detected waveforms of acoustically induced electromagnetic waves from a measurable object, showing at (a) waveform for Si crystal, and at (b) and (c) waveforms for GaAs crystals different in crystal arrangement.

FIG. 15 illustrates detected waveforms of acoustically induced electromagnetic waves from a measurable object 23, showing at (a) waveform for Si crystal, and at (b) and (c) waveforms for GaAs crystals different in crystal arrangement. In FIG. 15(a) to FIG. 15(c), the abscissa axis represents time (in μs) and the ordinate axis represents the signal intensity (in arbitrary scale).

From FIG. 15(a) where the measurable object is of Si, it is seen that no signal is detected. This is due to the fact that since Si is a single-element semiconductor, it does not exhibit a piezoelectric property.

FIG. 15(b) and FIG. 15(c) are shown that the ultrasonic wave number vector is oriented parallel to the (100) and (110) planes of GaAs crystal, respectively. When GaAs crystal is arranged to be excited by ultrasonic wave, it is seen that a high frequency signal is detected (see FIG. 15(c)).

The inserted figure in FIG. 15 is a graph illustrating a waveform of an electromagnetic wave signal generated from the GaAs crystal of FIG. 15(c) and transformed into a signal from a temporal range to a frequency range, specifically detected by the spectrum analyzer. In this inserted figure in FIG. 15, the abscissa axis represents the frequency (MHz) and the ordinate axis represents the signal intensity (arbitrary scale).

As is apparent from the inserted figure of FIG. 15, a high frequency signal of 7.60 MHz was observed. This high frequency signal occurred from the resonance oscillation waveform of ultrasonic waves of GaAs and had its Q (quality factor, also called voltage build-up rate) of about 10. The frequency of 7.60 MHz, with the acoustic propagation velocity in GaAs of 4730 m/s taken into account is presumed to be due to a mechanical resonance of one half wavelength corresponding to the thickness 350 μm of GaAs.

Example 4

As Example 4, acoustically induced electromagnetic waves from a rib of a pig were detected. The bone is made up of 70% of hydroxyapatite and 20% of a fiber consisting of oriented collagen, of which it is known that the fiber consisting of oriented collagen has a piezoelectric coefficient expressed by equation (8) below.

$$|d^{bone}| \approx 0.1 pC/N \qquad (8)$$

As the measurable object 23, a hard tissue of outer bone and a soft tissue of inner bone were prepared from a 2 mm thick square plate of bone cut out of the rib. The axis of the tissues was paralleled to the surface of the plate. Such specimens were ultrasonically cleaned with an ethanol solution for 1 hour. For all the specimens, the vector of ultrasonic waves is made perpendicular to the tissue axis. Ultrasonic pulses had a repetition frequency of 500 Hz to irradiate each of the bone specimens with ultrasonic waves via water for detection of electromagnetic waves. The gain of the small signal amplifier had set to 97 dB. And, the digital oscilloscope was used for 10 minutes for signal detection.

Figure 16:
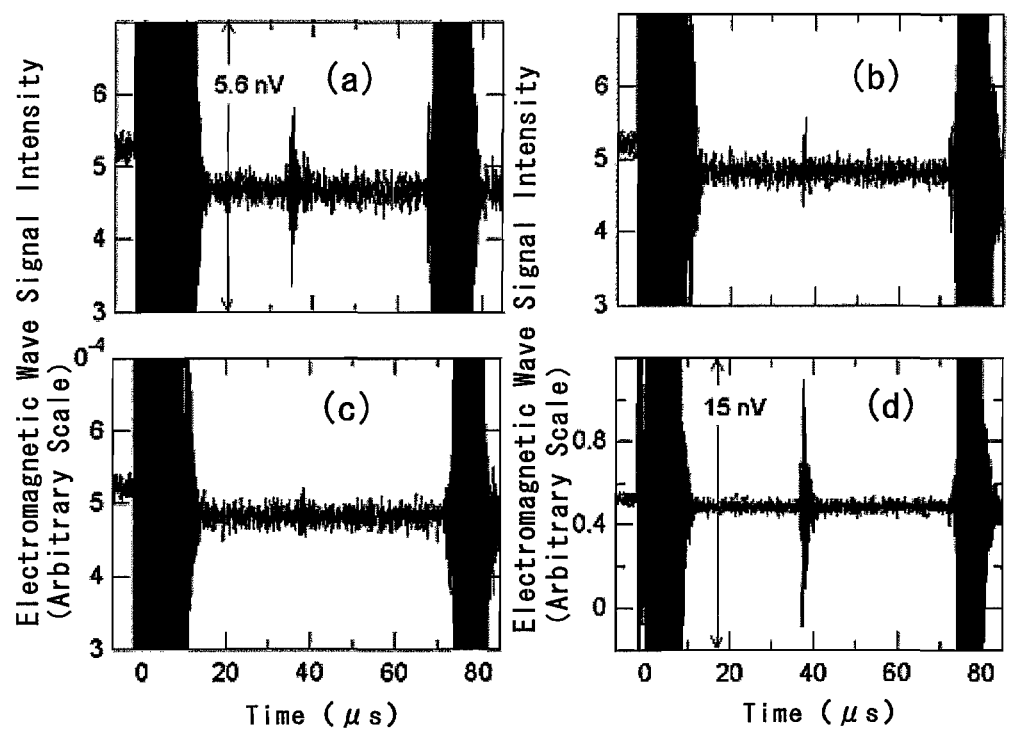
FIG. 16 illustrates detected waveforms in chart of acoustically induced electromagnetic waves, indicating at (a) a signal for hard osseous tissue of pig in Example 4, at (b) a signal for timber in Example 5, at (c) a signal for polypropylene in Example 6 and at (d) a signal for aluminum in Example 7.

FIG. 16(a) shows a detected waveform of acoustically induced electromagnetic waves from the hard tissue of pig's bone in Example 4, wherein the abscissa axis represents time (μs) and the ordinate axis represents the signal intensity (arbitrary scale).

As is apparent from FIG. 16(a) it is seen that electromagnetic waves can be detected from a hard tissue of a pig's bone. The soft tissue of pig's bone was likewise measured and a waveform of electromagnetic waves as in FIG. 16(a) could be detected. The piezoelectric coefficient of a bone has so far been reported to markedly damp in water with ion screening. As shown in Example 4, however, it was found that electromagnetic waves could be detected from a specimen of bone disposed in water. This indicates that the ion screening which is a phenomenon slower than in a MHz frequency band is negligible in the use of high frequency pulses of about 10 MHz level as in the present invention.

Example 5

As Example 5, electromagnetic waves from timber were detected, wherein the timber was irradiated with ultrasonic waves caused to propagate through a plastic tube (see FIG. 13(b)) as an ultrasonic probe. FIG. 16(b) is a chart illustrating a detected waveform of acoustically induced electromagnetic waves from timber in Example 5. In FIG. 16(b), the abscissa axis represents time (μs) and the ordinate axis represents the signal intensity (arbitrary scale). As is apparent from FIG. 16(b), it is seen that electromagnetic waves from timber can be detected. In this case it is presumed that timber which has cellulose as its main component which exhibits piezoelectricity brings about electromagnetic waves.

Example 6

As Example 6, acoustically induced electromagnetic waves were detected in a setup identical to that in Example 5 except that the measurable object 23 was of polypropylene as a plastic material.

FIG. 16(c) shows a detected waveform of acoustically induced electromagnetic waves from polypropylene in Example 6. In FIG. 16(c), the abscissa axis represents time (μs) and the ordinate axis represents the signal intensity (arbitrary scale). As is apparent from FIG. 16(c), it is seen that electromagnetic waves from polypropylene can be detected though its signal is extremely weak. In this case, it is presumed that polypropylene which is piezoelectric but feeble in signal output generates electromagnetic waves from crystallized grains.

Example 7

As Example 7, acoustically induced electromagnetic waves were detected in a setup identical to that in Example 5 except that the measurable object was of aluminum.

FIG. 16(d) shows a detected waveform of acoustically induced electromagnetic waves from aluminum in Example 7. In FIG. 16(d), the abscissa axis represents time (μs) and the ordinate axis represents the signal intensity (arbitrary scale). As is apparent from FIG. 16(d), it is seen that very strong electromagnetic waves from aluminum can be detected. In the case of aluminum in which the longitudinal waves in their acoustic mode change the bottom of a valence band via a potential modified interaction, it is presumed that electromagnetic waves are generated by this action causing the conduction electrons to be given a displacement repetitively.

Example 8

As Example 8, acoustically induced electromagnetic waves were detected in a setup identical to that in Example 5 except that the measurable object was of copper. As a result, it was found that very strong electromagnetic waves from copper as from aluminum could be detected.

Example 9

As Example 9, acoustically induced electromagnetic waves from ferrite magnets composed of SrO and $Fe_2O_3$ were detected.

Figure 17:
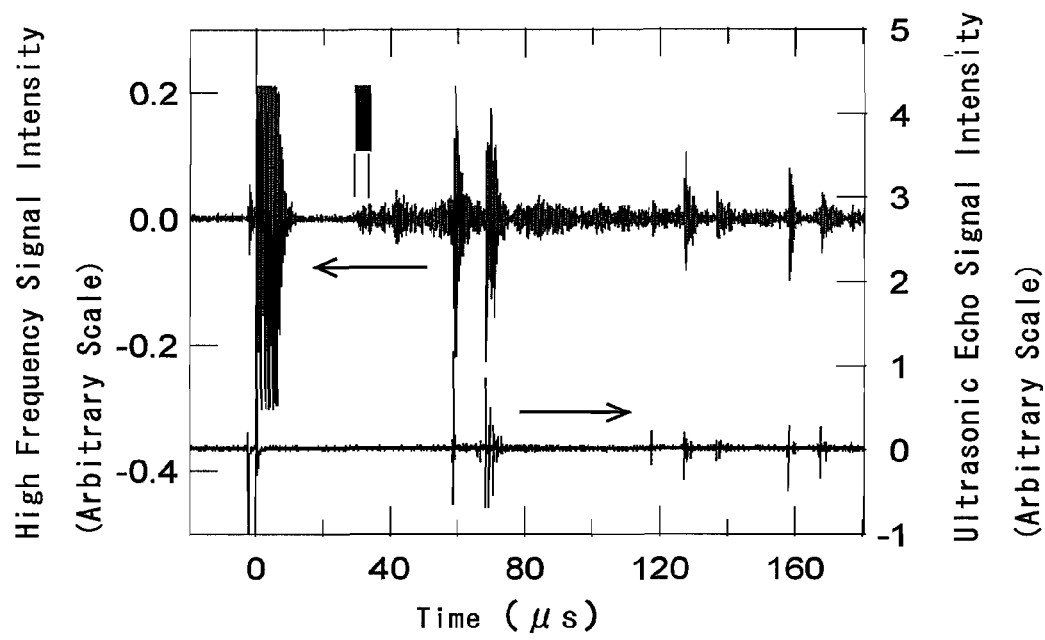
FIG. 17 is a chart of waveforms detected of acoustically induced electromagnetic waves from a ferrite magnet in Example 9.

FIG. 17 shows a detected waveform of acoustically induced electromagnetic waves from the ferrite magnet in Example 9. In FIG. 17, the abscissa axis represents time (μs) and the ordinate axis at the left hand side represents the intensity of high frequency signal of 8 MHz detected while the ordinate axis at the right hand side represents the intensity (arbitrary scale) of ultrasonic echo signal detected. It is seen that in a time range prior to arrival of acoustic waves at the specimen, the electromagnetic waves are low in noise level but subsequent to arrival of acoustic waves at the measurable object, the electromagnetic waves grows in background level over a long time. This suggests that the acoustic waves once entering inside of ferrite repeat reflection back and forth inside of the measurable object. As a result, it is presumed that the electromagnetic waves continue to be radiated over a time much longer than the acoustic waves are irradiated. Thus, from Example 9 it was found that acoustically induced electromagnetic waves could be detected from the measurable object if composed of a magnetic material, too.

The present invention is not limited to specific examples as mentioned above and allows various modifications within the scope of the invention set forth in the appended claims, which should, needless to say, fall within the scope of the invention.

INDUSTRIAL APPLICABILITY

As will be appreciated from the foregoing description, the use of a method and apparatus of the present invention in which a measurable object is irradiated with acoustic waves and electromagnetic waves emitted from the measurable object are measured, allows any of electric, magnetic and electromagnetic mechanical properties of the measurable object to be determined from one or a combination of intensity, phase and frequency characteristic of the electromagnetic waves.

Thus, as the electric property of a measurable object, a change or changes in one or more of property values for electric field, dielectric constant, spatial gradient of electric field and spatial gradient of dielectric constant, for concentration, mass, size, shape and number of charges of charged particles which the measurable object possesses and for interaction with a medium surrounding the charged particles can be measured. As the magnetic property of a measurable object, a property value for magnetization due to electron spin or nuclear spin in the measurable object or for acoustomagnetic resonance attributable to electron spin or nuclear spin in the measurable object can be measured. As the electromagnetic mechanical property of a measurable object, a piezoelectric property or magnetostriction property of said measurable object can be measured. Since a change or changes in one or more of property values for concentration, mass, size, shape and number of charges of charged particles which the measurable object possesses and for interaction with a medium surrounding the charged particles can thus be measured, measurement of a change or changes in these property values in a living body, colloidal solution, liquid crystal, solid electrolyte, ionic crystal, semiconductor, dielectric, metal, magnetic material and magnetic fluid or a composite material thereof or a structure or a functional device composed of such a material allows aiding in clarification of a related phenomenon. Especially, using the present invention in the determination of an active site in a brain makes it possible to identify an activated site at an extremely high position resolution and hence is extremely useful.

What is claimed is:

1. An apparatus to measure a property of an object with acoustically induced electromagnetic waves, comprising:
    an acoustic generator that emits an acoustic wave pulse towards the object, wherein the acoustic generator generates, upon emission of the acoustic wave pulse, electromagnetic noises, which are produced by the acoustic generator and which last after completing the emission of the acoustic wave pulse;
    a retainer table to hold the object at a prescribed distance from the acoustic generator such that a time period for the acoustic wave pulse to travel over the prescribed distance between the acoustic generator and the object is longer than duration of the electromagnetic noises which are in form of electromagnetic waves;
    means for receiving electromagnetic waves including induced electromagnetic waves which are induced from the object in response to the acoustic wave pulse, and the electromagnetic noises produced by the acoustic generator, the means for receiving electromagnetic waves first receiving the electromagnetic noises and subsequently receiving the induced electromagnetic waves, and the induced electromagnetic waves that are induced from the object in response to the acoustic wave pulse and the electromagnetic noises being separated in time from each other due to the prescribed distance; and
    a control, measure and process unit for driving and controlling the acoustic generator, wherein the control, measure and process unit measures and processes the induced electromagnetic waves that are induced from the object in response to the acoustic wave pulse and that are received by the means for receiving electromagnetic waves, and determines at least one of electric, magnetic, and electromagnetic/mechanical properties from one or a combination of intensity, phase and frequency characteristics of the induced electromagnetic waves that are induced from the object in response to the acoustic wave pulse.

2. The apparatus to measure a property of an object with acoustically induced electromagnetic waves as set forth in claim 1, wherein the acoustic generator comprises a plurality of acoustic generators or a plurality of acoustic generators fixed on a concaved surface whose normal is focused on a point,
    whereby acoustic wave pulses generated from the plurality of acoustic generators are controlled of their mutual phase by the control, measure and process unit to be focused on a desired position of the object, and a focusing position of acoustic wave pulse is scanned over a two-dimensional surface or three-dimensional volume of the object or the plurality of acoustic generators are scanned mechanically around the object to scan the focusing position of acoustic waves over a two-dimensional surface or three-dimensional volume of the object.

3. The apparatus to measure a property of an object with acoustically induced electromagnetic waves as set forth in any one of claims 1, 2, wherein the control, measure and process unit includes a Superconducting Quantum Interference Device (SQUID) for detecting a magnetic field.

4. The apparatus to measure a property of an object with acoustically induced electromagnetic waves as set forth in claim 1, wherein the control, measure and process unit includes means for heterodyne-detecting or means for phase-detecting the electromagnetic waves received by the means for receiving electromagnetic waves with a frequency of the acoustic wave pulse, and means for lock-in detecting an electromagnetic wave signal so detected with a pulse frequency of the acoustic wave pulse.

5. The apparatus to measure a property of an object with acoustically induced electromagnetic waves as set forth in claim 1, wherein the control, measure and process unit comprises means for causing broadband ultrashort pulses to be generated from the acoustic generator and means for measuring a frequency of the electromagnetic waves received by the means for receiving electromagnetic waves.

6. The apparatus to measure a property of an object with acoustically induced electromagnetic waves as set forth in claim 5, wherein the means for measuring a frequency of the electromagnetic waves comprises any one or a combination of a bandpass filter, a rock-in amplifier and a spectrum analyzer.

7. The apparatus to measure a property of an object with acoustically induced electromagnetic waves as set forth in any one of claims 1-2 and 4-6, wherein the object is a nervous tissue representative of a brain or a muscle tissue of a living body, and
    wherein the property, which can be determined by the control, measure and process unit, is a charge distribution formed when the neurons or muscle tissues are activated to identify a site of the neurons or muscle tissues that are activated.

8. The apparatus to measure a property of an object with acoustically induced electromagnetic waves as set forth in claim 7, wherein the control, measure and process unit includes a Superconducting Quantum Interference Device (SQUID) for detecting a magnetic field.

9. An apparatus to measure a property of an object with acoustically induced electromagnetic waves, comprising:

an acoustic generator that emits an acoustic wave pulse towards the object, a retainer table to hold the object at a prescribed distance from the acoustic generator such that a time period for the acoustic wave pulse to travel over the prescribed distance between the acoustic generator and the object is longer than a pulse duration of the acoustic wave pulse and that a relaxation of the induced electromagnetic waves that are induced from the object in response to the acoustic wave pulse occurs before echo noises in form of electromagnetic waves are produced by the acoustic generator in response to an echo of the acoustic wave pulse;

means for receiving electromagnetic waves including the induced electromagnetic waves and the echo noises; and a control, measure and process unit for driving and controlling the acoustic generator, wherein the control, measure and process unit measures and processes the induced electromagnetic waves that are induced from the object in response to the acoustic wave pulse and that are received by the means for receiving electromagnetic waves, and determines time dependency of intensities of the induced electromagnetic waves, wherein the control, measure and process unit determines a relaxation characteristic of a property value for charged particles of the object from the time dependency of the intensities of the induced electromagnetic waves before the echo noises due to the echo are produced.

* * * * *